United States Patent [19]

Gaster et al.

[11] Patent Number: 5,801,170

[45] Date of Patent: Sep. 1, 1998

[54] HETEROCYCLIC BIPHENYLYLAMIDES USEFUL AS 5HT1D ANTAGONISTS

[75] Inventors: Laramie Mary Gaster; Francis David King, both of Bishops Stortfield; Paul Adrian Wyman, Epping, all of England

[73] Assignee: SmithKline Beecham plc, Middlesex, England

[21] Appl. No.: 652,581

[22] PCT Filed: Nov. 28, 1994

[86] PCT No.: PCT/EP94/03948

§ 371 Date: Jun. 7, 1996

§ 102(e) Date: Jun. 7, 1996

[87] PCT Pub. No.: WO95/15954

PCT Pub. Date: Jun. 15, 1995

[30] Foreign Application Priority Data

Dec. 7, 1993 [GB] United Kingdom ............ 9325048
Mar. 26, 1994 [GB] United Kingdom ............ 9406044
May 7, 1994 [GB] United Kingdom ............ 9409083

[51] Int. Cl.$^6$ .............. C07D 271/06; C07D 271/10; A61K 31/41

[52] U.S. Cl. ............ 514/236.2; 514/326; 514/364; 544/138; 546/209; 548/131; 548/132; 548/133; 548/143; 548/144

[58] Field of Search .................. 548/131, 132, 548/133, 143, 144; 514/364, 235.8, 326, 236.2; 544/138; 546/209, 210

[56] References Cited

FOREIGN PATENT DOCUMENTS

| 0 533 267 A1 | 3/1993 | European Pat. Off. ...... C07D 213/56 |
| 0 533 268 A1 | 3/1993 | European Pat. Off. ...... C07D 271/06 |
| WO 94/15920 | 7/1994 | WIPO ...... C07D 231/12 |

OTHER PUBLICATIONS

Korolkovas, Essentials of Medicinal Chemistry, Second Edition, John Wiley & Sons, pp. 67–85, 1988.

*Primary Examiner*—Mukund J. Shah
*Assistant Examiner*—Deepak R. Rao
*Attorney, Agent, or Firm*—Soma G. Simon; Charles M. Kinzig; Edward T. Lentz

[57] ABSTRACT

A compound of formula (I) or a salt thereof:

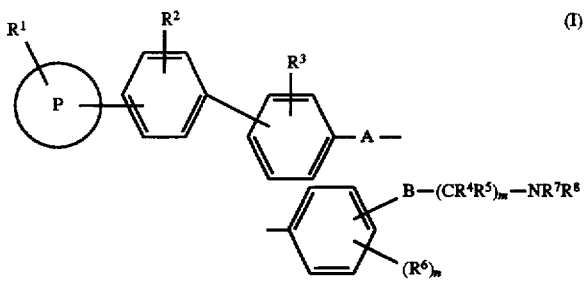

wherein P is a 5 to 7 membered heterocyclic ring selected from the group consisting of thienyl, furyl, pyrrolyl, triazolyl, diazolyl, tetrazolyl, imidazolyl, oxadiazolyl, isothiazolyl, isoxazolyl, thiadiazolyl, pyridyl, pyrimdyl and pyrazinyl;

$R^1$, $R^2$ and $R^3$ are independently hydrogen, halogen, $C_{1-6}$ alkyl, $C_{3-6}$ cycloalkyl, $C_{3-6}$ cycloalkenyl, $C_{1-6}$ alkoxy, hydroxy$C_{1-6}$ alkyl, $C_{1-6}$ alkylO$C_{1-6}$ alkyl, alkanoyl, optionally substituted phenyl, alkanoyloxy, hydroxy, nitro, trifluoromethyl, cyano, $CO_2R^9$, $CONR^{10}R^{11}$ where $R^9$, $R^{10}$ and $R^{11}$ are independently hydrogen or $C_{1-6}$ alkyl;

$R^4$ and $R^5$ are independently hydrogen or $C_{1-6}$ alkyl;

$R^6$ is hydrogen, halogen, hydroxy, $C_{1-6}$ alkyl or $C_{1-6}$ alkoxy $R^7$ and $R^8$ are independently hydrogen, $C_{1-6}$ alkyl, a optionally substituted phenylalkyl or together with the nitrogen atom to which they are attached form an optionally substituted 5- to 7-membered heterocyclic ring containing one or two heteroatoms selected from oxygen, nitrogen or sulphur;

A is CONH or NHCO;

B is oxygen, S(O)p where p is 0, 1 or 2, $NR^{12}$ where $R^{12}$ is hydrogen, $C_{1-6}$ alkyl or phenyl$C_{1-6}$ alkyl, or B is $CR^4$=$CR^5$ or $CR^4R^5$ where $R^4$ and $R^5$ are independently hydrogen or $C_{1-6}$ alkyl;

m is 1 to 4; and n is 1 or 2.

9 Claims, No Drawings

HETEROCYCLIC BIPHENYLYLAMIDES USEFUL AS 5HT1D ANTAGONISTS

This application is a 371 of PCT/EP94/03948 filed on Nov. 28, 1994.

The present invention relates to novel amide derivatives, processes for their preparation, and pharmaceutical compositions containing them.

EPA 0 533 266/7/8 disclose a series of benzanilide derivatives which are said to possess $5HT_{1D}$ receptor antagonist activity. These compounds are said to be of use in the treatment of various CNS disorders.

A structurally distinct class of compounds have now been discovered and have been found to exhibit $5HT_{1D}$ antagonist activity. In a first aspect, the present invention therefore provides a compound of formula (I) or a salt thereof:

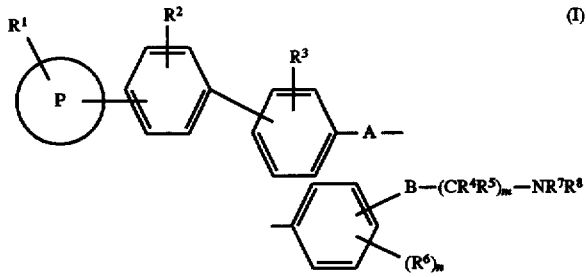

in which

P is a 5 to 7-membered heterocyclic ring containing 1 to 3 heteroatoms selected from oxygen, nitrogen or sulphur, $R^1$, $R^2$ and $R^3$ are independently hydrogen, halogen, $C_{1-6}$alkyl, $C_{3-6}$cycloalkyl, $C_{3-6}$cycloalkenyl, $C_{1-6}$alkoxy, hydroxy$C_{1-6}$alkyl, $C_{1-6}$alkyl$OC_{1-6}$alkyl, acyl, aryl, acyloxy, hydroxy, nitro, trifluoromethyl, cyano, $CO_2R^9$, $CONR^{10}R^{11}$, $NR^{10}R^{11}$ where $R^9$, $R^{10}$ and $R^{11}$ are independently hydrogen or $C_{1-6}$alkyl;

$R^4$ and $R^5$ are independently hydrogen or $C_{1-6}$alkyl;

$R^6$ is hydrogen, halogen, hydroxy, $C_{1-6}$alkyl or $C_{1-6}$alkoxy;

$R^7$ and $R^8$ are independently hydrogen, $C_{1-6}$alkyl, aralkyl, or together with the nitrogen atom to which they are attached form an optionally substituted 5- to 7-membered heterocyclic ring containing one or two heteroatoms selected from oxygen, nitrogen or sulphur;

A is CONH or NHCO;

B is oxygen, $S(O)_p$ where p is 0, 1 or 2, $NR^{12}$ where $R^{12}$ is hydrogen, $C_{1-6}$alkyl or phenyl$C_{1-6}$alkyl, or B is $CR^4$=$CR^5$ or $CR^4R^5$ where $R^4$ and $R^5$ are independently hydrogen or $C_{1-6}$alkyl;

m is 1 to 4; and n is 1 or 2.

$C_{1-6}$alkyl groups, whether alone or as part of another group, may be straight chain or branched.

Suitably P is a 5 to 7-membered heterocyclic ring containing 1 to 3 heteroatoms selected from oxygen, nitrogen or sulphur. Examples of suitable heterocyclic rings include thienyl, furyl, pyrrolyl, triazolyl, diazolyl, imidazolyl, oxadiazolyl, isothiazolyl, isoxazolyl, thiadiazolyl, pyridyl, pyrimidyl and pyrazinyl. The heterocyclic rings can be linked to the remainder of the molecule via a carbon atom or, when present, a nitrogen atom. Preferably P is oxadiazolyl.

Suitably $R^1$, $R^2$ and $R^3$ are independently hydrogen, halogen, $C_{1-6}$alkyl, $C_{3-6}$cycloalkyl, $C_{3-6}$cycloalkenyl, $C_{1-6}$alkoxy, hydroxy$C_{1-6}$alkyl, $C_{1-6}$alkyl$OC_{1-6}$alkyl, acyl, aryl, acyloxy, hydroxy, nitro, trifluoromethyl, cyano, $CO_2R^9$, $CONR^{10}R^{11}$, $NR^{10}R^{11}$ where $R^9$, $R^{10}$ and $R^{11}$ are independently hydrogen or $C_{1-6}$alkyl. Preferably $R^1$ and $R^2$ are $C_{1-6}$alkyl, in particular methyl. Preferably $R^3$ is hydrogen.

Suitably $R^4$ and $R^5$ are independently hydrogen or $C_{1-6}$alkyl. Preferably $R^4$ and $R^5$ are both hydrogen.

Suitably $R^7$ and $R^8$ are independently hydrogen, $C_{1-6}$alkyl, aralkyl, or together with the nitrogen atom to which they are attached form an optionally substituted 5- to 7-membered heterocyclic ring containing one or two heteroatoms selected from oxygen, nitrogen or sulphur. Examples of $R^7$ and $R^8$ as heterocyclic rings include pyrrolidine, morpholine, piperazine and piperidine. Optional substituents for such rings include $C_{1-6}$alkyl. Preferably $R^7$ and $R^8$ are both $C_{1-6}$alkyl, in particular methyl.

Suitably $R^6$ is hydrogen, halogen, hydroxy, $C_{1-6}$alkyl or $C_{1-6}$alkoxy. Preferably $R^6$ is $C_{1-6}$alkoxy such as methoxy.

Suitably A is CONH or NHCO. Preferably A is CONH.

Suitably B is oxygen, $S(O)_p$ where p is 0, 1 or 2, $NR^{12}$ where $R^{12}$ is hydrogen, $C_{1-6}$alkyl or phenyl$C_{1-6}$alkyl, or B is $CR^4$=$CR^5$ or $CR^4R^5$ where $R^4$ and $R^5$ are independently hydrogen or $C_{1-6}$alkyl. Preferably B is oxygen, $CH_2$ or $NR^{12}$ where $R^{12}$ is phenyl$C_{1-6}$alkyl such as phenethyl.

Suitably m is 1 to 4, preferably m is 2

Suitably n is 1 or 2, preferably n is 1.

The groups $-B(CR^4R^5)_m NR^7R^8$ and $R^6$ can be attached to the phenyl ring at any suitable position. Preferably the group $-B(CR^4R^5)_m NR^7R^8$ is meta to the amide linkage and the group $R^6$ is para to the amide linkage. The groups $R^1$, $R^2$ and $R^3$ can be attached to their respective rings at any suitable position.

Particularly preferred compounds of the invention include:

N-[3-(Dimethylaminoethoxy)-4-methoxyphenyl]-2'-methyl-4'-(5-methyl-1,2,4-oxadiazol-3-yl)biphenyl-4-carboxamide, N-[3-(2-Diethylaminoethoxy)-4-methoxyphenyl]-2'-methyl-4'-(5-methyl-1,2,4-oxadiazol-3-yl)biphenyl-4-carboxamide, N-[3-(2-Diisopropylaminoethoxy)-4-methoxyphenyl]-2'-methyl-4'-(5-methyl-1,2,4-oxadiazol-3-yl)biphenyl-4-carboxamide, N-[3-(2-Dimethylamino-1-methylethoxy)-4-methoxyphenyl]-2'-methyl-4'-(5-methyl-1,2,4-oxadiazol-3-yl)biphenyl-4-carboxamide, N-[3-(2-Dimethylaminopropoxy)-4-methoxyphenyl]-2'-methyl-4'-(5-methyl-1,2,4-oxadiazol-3-yl)biphenyl-4-carboxamnide, N-[3-(2-Methylaminoethoxy)-4-methoxyphenyl]-2'-methyl-4'-(5-methyl-1,2,4-oxadiazol-3-yl)biphenyl-4-carboxamide, N-[3-(2-Aminoethoxy)-4-methoxyphenyl]-2'-methyl-4'-(5-methyl-1,2,4-oxadiazol-3-yl)biphenyl-4-carboxamide, N-[3-(2-Piperidin-1-ylethoxy)-4-methoxyphenyl]-2'-methyl-4'-(5-methyl-1,2,4-oxadiazol-3-yl)biphenyl-4-carboxamide, N-[3-(2-Morpholin-4-ylethoxy)-4-methoxyphenyl]-2'-methyl-4'-(5-methyl-1,2,4-oxadiazol-3-yl)biphenyl-4-carboxamide, N-[3-(2-Dimethylaminoethoxy)-4-methoxyphenyl]-2'-methyl-4'-(3-methyl-1,2,4-oxadiazol-5-yl)biphenyl-4-carboxamide, N-[3-(2-Dimethylaminoethoxy)-4-methoxyphenyl]-2'-methyl-4'-(5-methyl-1,3,4-oxadiazol-2-yl) biphenyl-4-carboxamide, N-[3-(2-Dimethylaminoethoxy)-4-methoxyphenyl]-2'-methyl-4'-(1,3,4-oxadiazol-2-yl)biphenyl-4-carboxamide, N-[3-(2-Dimethylaminoethoxy)phenyl]-2'-methyl-4'-(5-methyl-1,2,4-oxadiazol-3-yl)biphenyl-4-carboxamide, N-[5-(2-Dimethylaminoethoxy)-2,4-diiodophenyl]-2'-methyl-4'-(5-methyl-1,2,4-oxadiazol-3-yl)biphenyl-4-carboxamide, N-[3-[(2-Dimethylaminoethyl)amino]-4-methoxyphenyl]-2'-methyl-4'-(5-methyl-1,2,4-oxadiazol-3-yl)-biphenyl-4-carboxamide, N-[3-(3-Dimethylaminopropoxy)-4-methoxyphenyl]-2'-methyl-4'-(5-methyl-1,2,4-oxadiazol-3-yl)biphenyl-4-carboxamide, N-[3-(3-Dimethylaminopropyl)-4-methoxyphenyl]-2'-methyl-4'-(5-methyl-1,2,4-oxadiazol-3-yl)biphenyl-4-carboxamide, N-[3-(3-Dimethylaminoprop-1-enyl)-4-methoxyphenyl]-2'-methyl-4'-(5-methyl-1,2,4-oxadiazol-3-yl)biphenyl-4-carboxamide, N-[4-(3-Dimethylaminopropoxy)phenyl]-2'-methyl-4'-(5-methyl-1,2,4-oxadiazol-3-yl)biphenyl-4-carboxamide, N-[3-(2-Pyrrolidin-1-ylethoxy)-4-methoxyphenyl]-2'-methyl-4'-(5-methyl-1,2,4-oxadiazol-3-yl)biphenyl-4-carboxamide, N-[3-(2-Dimethylaminoethoxy)-4-methoxyphenyl]-2'-methyl-4'-(5-ethyl-1,2,4-oxadiazol-3-yl)biphenyl-4-carboxamide, N-[3-(2-Dimethylaminoethoxy)-4-methoxyphenyl]-2'-methyl-4'-(5-dimethylamino-1,2,4-oxadiazol-3-yl)biphenyl-4-carboxamide, N-[3-(2-Dimethylaminoethoxy)-4-methoxyphenyl]-2'-methyl-4'-(4-methylthiazol-2-yl)biphenyl-4-carboxamide, N-[3-(2-Dimethylaminoethoxy)-4-methoxyphenyl]-2'-methyl-4'-pyrazinyl biphenyl-4-carboxamide, N-[3-(2-Dimethylaminoethylthio)-4-methoxyphenyl]-2'-methyl-4'-(5-methyl-1,2,4-oxadiazol-3-yl)biphenyl-4-carboxamide, N-[3-(2-Dimethylaminoethylsulphinyl)-4-methoxyphenyl]-2'-methyl-4'-(5-methyl-1,2,4-oxadiazol-3-yl)biphenyl-4-carboxamide, N-[5-(2-Dimethylaminoethoxy)-2-chlorophenyl]-2'-methyl-4'-(5-methyl-1,2,4-oxadiazol-3-yl)biphenyl-4-carboxamide, N-[3-(2-Dimethylaminoethoxy)-4-chlorophenyl]-2'-methyl-4'-(5-methyl-1,2,4-oxadiazol-3-yl)biphenyl-4-carboxamide, N-[3-(2-Dimethylaminoethoxy)-4-bromophenyl]-2'-methyl-4'-(5-methyl-1,2,4-oxadiazol-3-yl)biphenyl-4-carboxamide, N-[3-(2-Dimethylaminoethoxy)-4-iodophenyl]-2'-methyl-4'-(5-methyl-1,2,4-oxadiazol-3-yl)biphenyl-4-carboxamide, N-[3-(2-Dimethylaminoethoxy)-4-ethylphenyl]-2'-methyl-4'-(5-methyl-1,2,4-oxadiazol-3-yl)biphenyl-4-carboxamide, N-[3-(2-Dimethylaminoethoxy)-4-isopropylphenyl]-2'-methyl-4'-(5-methyl-1,2,4-oxadiazol-3-yl)biphenyl-4-carboxamide, N-[3-(2-Dimethylaminoethoxy)-4-methoxyphenyl]4'-(1,2,4-triazol-1-yl)-2'-methyl-(1,1'-biphenyl)-4-carboxamide, N-[3-(2-Dimethylaminoethoxy)-4-methoxyphenyl]-4'-(5-methyl-1,2,4-oxadiazol-3-yl)-1,1'-biphenyl-4-carboxamide, N-[3-(2-Dimethylaminoethoxy)-4-methoxyphenyl]-4'-(1,2,4-triazol-1-yl)-1,1'-bipheny-4-carboxamide, N-[3-(2-Dimethylaminoethoxy)-4-methoxyphenyl]-4'-(tetrazol-2-yl)-1,1'-biphenyl-4-carboxamide, N-[3-(2-Dimethylaminoethoxy)-4-methoxyphenyl]-2-methyl-4'-(5-methyl-1,2,4-oxadiazol-3-yl)-1,1'-biphenyl-4-carboxamide, N-[3-(2-Dimethylaminoethoxy)-4-methoxyphenyl]-2-methyl-4'-(2-pyridyl)-1,1'-biphenyl-4-carboxamide, N-[3-(2-Dimethylaminoethoxy)-4-methoxyphenyl]-2-methyl-4'-(3-pyridyl)-1,1'-biphenyl-4-carboxamide, N-[3-(2-Dimethylaminoethoxy)-4-methoxyphenyl]-2'-ethyl-4'-(5-methyl-1,2,4-oxadiazol-3-yl)-1,1'-biphenyl-4-carboxamide, N-[3-(2-Dimethylarminoethoxy)-4-methoxyphenyl]-2,2'dimethyl-4'-(5-methyl-1,2,4-oxadiazol-3-yl)-1,1'-biphenyl-4-carboxamide, N-[3-(N'-(2-Dimethylaminoethyl)-N'-methylamino)-4-methoxyphenyl]-2'-methyl-4'-(5-methyl-1,2,4-oxadiazol-3-yl)-1,1'-biphenyl-4-carboxamide N-[3-(N'-(2-Dimethylaminoethoxy)-N'-phenethylamino)-4-methoxyphenyl]-2'-methyl-4'-(5-methyl-1,2,4-oxadiazol-3-yl)-1,1'-biphenyl-4-carboxamide, N-[3-(N'-(2-Dimethylaminoethoxy)-N'-butylamino)-4-methoxyphenyl]-2'-methyl-4'-(5-methyl-1,2,4-oxadiazol-3-yl)-1,1'-biphenyl-4-carboxamide, N-[3-(2-Dimethylaminoethoxy)-4-methoxyphenol]-4'-(1,2,4-triazol-1-yl)-(1,1'-biphenyl) -4-carboxamide, N-[3-(2-Dimethylaminoethoxy)-4-methoxyphenol]-4'-(tetrazol-2-yl)-(1,1'-biphenyl)-4-carboxamide, N-[3-(2-Dimethylaminoethoxy)-4-methoxyphenol]-2'-methyl-4'-(1,2,4-triazol-1-yl)-(1,1'-biphenyl)-4-carboxamide, or pharmaceutically acceptable salts thereof.

Preferred salts of the compounds of formula (I) are pharmaceutically acceptable salts. These include acid addition salts such as hydrochlorides, hydrobromides, phosphates, acetates, fumarates, maleates, tartrates, citrates, oxalates, methanesulphonates and p-toluenesulphonates.

Certain compounds of formula (I) are capable of existing in stereoisomeric forms. It will be understood that the invention encompasses all geometric and optical isomers of the compounds of formula (I) and the mixtures thereof including racemates. Tautomers and mixtures thereof also form an aspect of the invention.

In a further aspect the present invention provides a process for the preparation of a compound of formula (I) which comprises.

(a) reaction of a compound of formula (II):

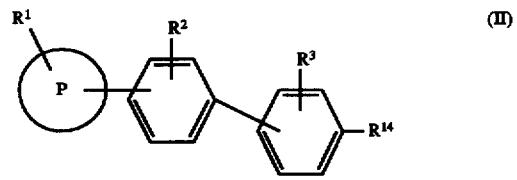

with a compound of formula (III):

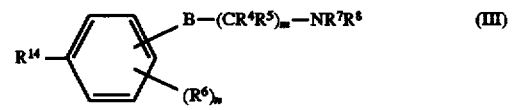

wherein B, m, n, P, $R^1$, $R^2$, $R^3$, $R^4$, $R^5$, $R^6$, $R^7$ and $R^8$ are as defined in formula (I) and $R^{13}$ and $R^{14}$ contain the appropriate functional group(s) necessary to form the A moiety; and optionally thereafter in any order:

converting a compound of formula (I) into another compound of formula (I)

forming a pharmaceutically acceptable salt.

Suitably one of $R^{13}$ or $R^{14}$ is an activated carboxylic acid derivative, such as an acyl halide or acid anhydride, and the other is an amine group. Activated compounds of formulae (II) or (III) can also be prepared by reaction of the corresponding carboxylic acid with a coupling reagent such as carbonyldiimidazole, dicyclohexylcarbodiimide or diphenylphosphorylazole. Preferably $R^{13}$ or $R^{14}$ is a group COL where L is halo, particularly chloro.

A compound of formulae (II) and (III) are typically reacted together in an inert organic solvent such as DMF, TBF or dichloromethane at ambient or elevated temperature in the presence of a base such as an alkali metal hydroxide, triethylamine or pyridine.

Intermediate compounds of formulae (II) and (III) are commercially available or can be prepared using standard procedures such as those outlined in EPA 533266/7/8. Certain intermediate compounds of formulae (II) and (III) are novel and form a further aspect of the invention.

It will be appreciated to those skilled in the art that it may be necessary to protect certain reactive substituents during some of the above procedures. Standard protection and deprotection techniques can be used. For example, primary amines can be protected as phthalimide, benzyl, benzyloxycarbonyl or trityl derivatives. These groups can be removed by conventional procedures well known in the art.

Carboxylic acid groups can be protected as esters. Aldehyde or ketone groups can be protected as acetals, ketals, thioacetals or thioketals. Deprotection is achieved using standard conditions.

Certain compounds of formula (I) can be converted into further compounds of formula (I) using standard processes. For example compounds in which $R^7$ and $R^8$ are both hydrogen or one of $R^7$ or $R^8$ is hydrogen and the other is $C_{1-6}$alkyl can be converted to compounds in which $R^7$ and $R^8$ are both $C_{1-6}$alkyl using standard alkylation techniques.

$5HT_{1D}$ Antagonists, and in particular the compounds of the present invention, are expected to be of use in the treatment of CNS disorders such as mood disorders, including depression, seasonal effective disorder and dysthymia; anxiety disorders, including generalised anxiety, panic disorder, agoraphobia, social phobia, obsessive compulsive disorder and post-traumatic stress disorder; memory disorders, including dementia, amnestic disorders and age-associated memory impairment; and disorders of eating behaviours, including anorexia nervosa and bulimia nervosa. Other CNS disorders include Parkinson's disease, dementia in Parkinson's disease, neuroleptic-induced Parkinsonism and tardive dyskinesias, as well as other psychiatric disorders.

$5HT_{1D}$ Antagonists, and in particular compounds of the present invention, may also be of use in the treatment of endocrine disorders such as hyperprolactinaemia, in the treatment of vasospasm (particularly in the cerebral vasculature) and hypertension, as well as disorders in the gastrointestinal tract where changes in motility and secretion are involved. They may also be of use in the treatment of sexual dysfunction and hypothermia.

Therefore, the present invention, provides a compound of general formula (I) or a physiologically acceptable salt or solvate thereof for use in therapy.

The present invention also provides a compound of general formula (I) or a physiologically acceptable salt or solvate thereof for use in the treatment of the aforementioned disorders.

In another aspect the invention provides the use of a compound of general formula (I) or a pharmaceutically acceptable salt or solvate thereof for the manufacture of a medicament for the treatment of the aforementioned disorders.

In a further aspect the invention provides a method of treating the aforementioned disorders which comprises administering an effective amount to a patient in need of such treatment of a compound of general formula (I) or a pharmaceutically acceptable salt or solvate thereof.

In particular the invention provides a compound of general formula (I) or a physiologically acceptable salt or solvate thereof for use in the treatment or prophylaxis of depression.

It will be appreciated by those skilled in the art that the compounds according to the invention may advantageously be used in conjunction with one or more other therapeutic agents, for instance, different antidepressant agents.

The present invention also provides a pharmaceutical composition, which comprises a compound of formula (I) or a pharmaceutically acceptable salt thereof, and a pharmaceutically acceptable carrier.

A pharmaceutical composition of the invention, which may be prepared by admixture, suitably at ambient temperature and atmospheric pressure, is usually adapted for oral, parenteral or rectal administration and, as such, may be in the form of tablets, capsules, oral liquid preparations, powders, granules, lozenges, reconstitutable powders, injectable or infusible solutions or suspensions or suppositories. Orally administrable compositions are generally preferred.

Tablets and capsules for oral administration may be in unit dose form, and may contain conventional excipients, such as binding agents, fillers, tabletting lubricants, disintegrants and acceptable wetting agents. The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents, emulsifying agents, non-aqueous vehicles (which may include edible oils), preservatives, and, if desired, conventional flavourings or colorants.

For parenteral administration, fluid unit dosage forms are prepared utilising a compound of the invention or pharmaceutically acceptable salt thereof and a sterile vehicle. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilisation cannot be accomplished by filtration. The compound can be sterilised by exposure to ethylene oxide before suspension in a sterile vehicle. Advantageously, a surfactant or wetting agent is included in the composition to facilitate uniform distribution of the compound.

The composition may contain from 0.1% to 99% by weight, preferably from 10 to 60% by weight, of the active material, depending on the method of administration.

The dose of the compound used in the treatment of the aforementioned disorders will vary in the usual way with the seriousness of the disorders, the weight of the sufferer, and other similar factors. However, as a general guide suitable unit doses may be 0.05 to 1000 mg, more suitably 1.0 to 200 mg, and such unit doses may be administered more than once a day, for example two or three a day. Such therapy may extend for a number of weeks or months.

The following Examples illustrate the preparation of compounds of the invention.

DESCRIPTION 1
2-(Dimethylaminoethoxy)-4-nitroanisole

A stirred solution of 2-methoxy-5-nitrophenol (5.0 g, 0.029 mole) and potassium carbonate (8.3 g, 0.060 mole) in acetone (200 ml) and water (60 ml) was treated with N,N-dimethylaminoethyl chloride hydrochloride (8.64 g, 0.060 mole) and heated under reflux for 10 h. The mixture was concentrated under vacuum to approx. 80 ml volume, then acidified with 2M HCl acid (150 ml) and washed with ethyl acetate (2×80 ml). The acid solution was basified with $K_2CO_3$ and extracted with ethyl acetate (2×100 ml). The combined extract was dried ($Na_2SO_4$) and concentrated under vacuum to afford the title compound as a yellow solid (4.87 g, 70%).

$^1$H NMR (250 MHz) $CDCl_3$ δ: 7.92 (1H, dd), 7.77 (1H, d), 6.91 (1H, d), 4.18 (2H, t), 3.96 (3H, s), 2.82 (2H, t), 2.37 (6H, s).

DESCRIPTION 2
2-(Dimethylaminoethoxy)-4-methoxyaniline

A solution of 2-(dimethylaminoethoxy)-4-nitroanisole (D1, 4.8 g, 0.020 mole) in ethanol (200 ml) was hydrogenated over 10% Pd-C (0.5 g) at room temperature and pressure. When reduction was complete (1 h), the catalyst was removed by filtration through kieselguhr and the filtrate concentrated under vacuum to afford the title compound as a pink solid (4.0 g, 95%).

$^1$H NMR (250 MHz) $CDCl_3$ δ: 6.71 (1H, d), 6.33 (1H, d), 6.24 (1H, dd), 4.07 (2H) 3.78 (3H, s), 3.46 (2H, br s), 2.76 (2H, t), 2.33 (6H, s)

DESCRIPTION 3
3-(2-Diethylaminoethoxy)-4-methoxyaniline

The title compound was prepared from 2-methoxy-5-nitrophenol and 2-diethylaminoethyl chloride hydrochloride using a similar procedure to Descriptions 1 and 2 (71%).

$^1$H NMR (200 MHz, $CDCl_3$) δ(ppm): 6.73 (d, 1H), 6.36 (brd, 1H), 6.27 (dd, 1H 4.08 (t, 2H), 3.83 (s, 3H), 3.53 (s, 2H), 2.96 (t, 2H), 2.67 (q, 4H), 1.10 (t, 6H).

DESCRIPTION 4
3-(2-Diisopropylaminoethoxy)-4-methoxyaniline

The title compound was prepared from 2-methoxy-5-nitrophenol and 2-diisopropylaminoethyl chloride hydrochloride, following a procedure similar to that described in Descriptions 1 and 2 (81%).

$^1$H NMR (250 MHz; $CDCl_3$) δ(ppm): 6.70 (d, 1H), 6.32 (d, 1H), 6.22 (dd, 1H), 3.89 (t, 2H), 3.80 (s, 3H), 3.44 (brs, 2H), 3.19–2.99 (m, 2H), 2.89 (t, 2H), 1.05 (d, 12H)

DESCRIPTION 5
2-(2-Dimethylamino-1-methylethoxy)-4-nitroanisole and 2-(2-dimethylaminopropoxy)-4-nitroanisole 2-Methoxy-5-nitrophenol was reacted with 2-dimethylaminoisopropyl chloride hydrochloride using a similar procedure to Description 1. Purification of the product mixture by chromatography on silica gel eluting with 5% methanol/dichloromethane afforded 2-(2-dimethylaminoisopropoxy)-4-nitroanisole (D5a) (0.32 g, 21%)

$^1$H NMR (200 MHz, $CDCl_3$) δ(ppm): 7.90 (dd, 1H), 7.81 (d, 1H), 6.90 (d, 1H), 4.59 (sextet, 1H), 3.94 (s, 3H), 2.74 (dd, 1H), 2.47 (dd, 1H), 2.32 (s, 6H), 1.37 (d, 3H), and 2-(2-dimethylaminopropoxy)-4-nitroanisole (D5b) (0.13 g, 9%)

$^1$H NMR (250 MHz, $CDCl_3$) δ(ppm): 7.92 (dd, 1H), 7.76 (d, 1H), 6.92 (d, 1H) 4.16 (dd, 1H), 3.96 (s, 3H), 3.90 (dd, 1H), 3.10 (sextet, 1H), 2.28 (s, 6H), 1.18 (d, 3H)

DESCRIPTION 6
3-(2-Dimethylamino-1-methylethoxy)-4-methoxyaniline

The title compound was prepared from 2-(2-dimethylamino-1-methylethoxy)-4-nitroanisole (D5a) using a similar procedure to Description 2 (89%).

$^1$H NMR (250 MHz, $CDCl_3$) δ(ppm): 6.72 (d, 1H), 6.38 (d, 1H), 6.27 (dd, 1H), 4.47 (sextet, 1H), 3.77 (s, 3H), 3.2 (brs, 2H), 2.72 (dd, 1H), 2.47 (dd, 1H), 2.33 (s,6H), 1.32 (d, 3H)

DESCRIPTION 7
3-(2-Dimethylaminopropoxy)-4-methoxyaniline

The title compound was prepared from 2-(2-dimethylaminopropoxy)-4-nitroanisole (D5b) using a similar procedure to Description 2 (91%).

$^1$H NMR (250 MHz, $CDCl_3$) δ(ppm): 6.63 (d, 1H), 6.25 (d, 1H), 6.17 (dd, 1H) 3.99 (dd, 1H), 3.70 (s, 3H) and (dd, 1H), 3.38 (brs, 2H), 2.96 (sextet, 1H), 2.28 (s, 6H), 1.07 (d, 3H)

DESCRIPTION 8
2-Cyanomethoxy-4-nitroanisole

A stirred solution of 2-methoxy-5-nitrophenol (2 g, 0.012 mole) and potassium carbonate (1.64 g, 0.012 mole) in acetone (10 ml) was treated with bromoacetonitrile (0.19 ml, 0.013 mole) in acetone (10 ml) and stirred for 3 hours at room temperature. The mixture was concentrated in vacuo and the residue treated with 10% NaOH solution, then extracted with ethyl acetate. The organic extract was dried ($Na_2SO_4$) and evaporated in vacuo to give the title compound (2.35 g, 96%).

$^1$H NMR (250 MHz, $CDCl_3$) δ(ppm): 8.10 (dd, 1H), 7.94 (d, 1H), 7.03 (d, 1H), 4.92 (s, 2H), 4.00 (s, 3H)

DESCRIPTION 9
2-(2-Aminoethoxy)-4-nitroanisole

To a suspension of sodium borohydride (0.55 g, 0.015 mole) in dry THF (50 ml) at 0° C., under an argon atmosphere, was added boron trifluoride etherate (2.4 ml, 0.02 mole) dropwise. After addition was completed the mixture was left to stir for 1 hour at room temperature and then a solution of 2-cyanomethoxy-4-nitroanisole (D8 1.0 g, 0,0048 mole) in dry THF (50 ml) was added and the mixture heated under reflux for 1 hour. The mixture was treated with saturated aqueous $NaHCO_3$ solution until effervescence had ceased and then concentrated in vacuo. The residue was treated with water and extracted with dichloromethane. The combined organic extracts were dried and concentrated in vacuo to give the title compound (1.0 g, 100%).

$^1$H NMR (250 MHz, $CDCl_3$) δ(ppm): 7.95 (dd, 1H), 7.78 (d, 1H), 6.92 (d, 1H), 4.12 (t, 2H), 3.97 (s, 3H), 3.19 (t, 2H), 1.61 (brs, 2H)

DESCRIPTION 10
2-(2-(t-butyloxycarbonylamino)ethoxy)-4-nitroanisole

A stirred solution of 2-(2-aminoethoxy)-4-nitroanisole (D9, 0.2 g, 1.1 mmole) in dichloromethane (5 ml) was treated initially with triethylamine (0.28 ml, 2 mmole) followed by a solution of di-t-butyl dicarbonate (0.21 g, 0.91 mmole) in dichloromethane (5 ml). The mixture was allowed to stir at room temperature for 3 hours, then treated with 10% $Na_2CO_3$ solution and extracted with dichloromethane. The organic layer was dried ($Na_2SO_4$) and evaporated in vacuo to afford the title compound as a pale yellow solid (1.05 g, 70%).

¹H NMR (250 MHz, CDCl₃) δ(ppm): 7.95 (dd, 1H), 7.77 (d, 1H), 6.92 (d, 1H), 5.10 (brs, 1H), 4.15 (t, 2H), 3.98 (s, 3H), 3.64–3.58 (m, 2H), 1.49 (s, 9H).

DESCRIPTION 11
3-(2-(t-Butyloxycarbonylamino)ethoxy)-4-methoxyaniline

The title compound was prepared from 2-(2-(t-butyloxycarbonylamino)-ethoxy-4-nitroanisole (D10) following a procedure similar to that described in Description 2 (93%).

¹H NMR (250 MHz, CDCl₃) δ(ppm): 6.72 (d, 1H), 6.31 (d, 1H), 6.28 (dd, 1H), 5.35 (brs, 1H), 4.01 (t, 2H), 3.79 (s, 3H), 3.50 (t, 2H), and (brs, 2H), 1.47 (s, 9H)

DESCRIPTION 12
3-(2-Piperidin-1-ylethoxy)-4-methoxyaniline

The title compound was prepared from 2-methoxy-5-nitrophenol and 1-(2-chloroethyl)piperidine hydrochloride using a similar procedure to Descriptions 1 and 2 (40%).

¹H NMR (250 MHz, CDCl₃) δ(ppm): 6.62 (d, 1H), 6.25 (d, 1H), 6.15 (dd, 1H), 4.04 (t, 2H), 3.70 (s, 3H), 3.37 (brs, 2H), 2.73 (t, 2H), 2.50–2.37 (m, 4H), 1.60–1.30 (m, 6H).

DESCRIPTION 13
3-(2-Morpholin-4-ylethoxy)-4-methoxyaniline

The title compound was prepared from 2-methoxy-5-nitrophenol and 4-(2-chloroethyl)morpholine hydrochloride using a similar procedure to Descriptions 1 and 2 (63%).

¹H NMR (250 MHz, CDCl₃) δ(ppm): 6.72 (d, 1H), 6.33 (d, 1H), 6.25 (dd, 1H), 4.12 (t, 2H), 3.78 (s, 3H), 3.75–3.68 (m, 4H), 3.44 (brs, 2H), 2.83 (t, 2H), 2.65–2.54 (m, 4H)

DESCRIPTION 14
4'-Methoxycarbonyl-2'-methylbiphenyl-4-carboxylic acid

A stirred solution of methyl 4-bromo-3-methylbenzoate (EP 0533268 A1) (1.0 g, 0.0044 mole) in dry DMF (10 ml) under argon was treated with 4-boronobenzoic acid (0.73 g, 0.0044 mole) and tetrakis (triphenylphosphine)palladium(0) (80 mg), followed by triethylamine (1.8 ml, 0.016 mole). The mixture was heated at 100° C. for 18 hours, then concentrated in vacuo. The residue was treated with ethyl acetate and extracted with 10% NaHCO₃ solution. The basic extract was acidified with dil. HCl and extracted with ethyl acetate. The extract was dried (Na₂SO₄) and concentrated in vacuo to afford the title compound as a white solid (0.46 g, 39%).

¹H NMR (250 MHz, d⁶DMSO: δ(ppm): 13.1 (brs, 1H), 8.04 (d, 2H), 7.93 (s, 1H), 7.87 (d, 1H), 7.51 (d, 2H), 7.38 (d, 1H), 3.87 (s, 3H), 2.30 (s, 3H)

DESCRIPTION 15
2'-Methyl-4'-(3-methyl-1,2,4-oxadiazol-5-yl)biphenyl-4-carboxylic acid A stirred solution of 5-(4-bromo-3-methylphenyl)-3-methyl-1,2,4-oxadiazole (EP 0533268 A1) (0.65 g, 0.0026 mole) in a mixture of DME (30 ml) and water (30 ml) under argon was treated with 4-boronobenzoic acid (0.43 g, 0.0026 mole), sodium carbonate (1.16 g, 0.011 mole) and tetrakis (triphenylphosphine)palladium(0) (40 mg), then heated under reflux for 4 hours. The mixture was acidified with 1M hydrochloric acid and extracted with ethyl acetate. The extract was dried (Na₂SO₄) and concentrated in vacuo to leave the title compound as a white solid (0.61 g, 80%).

¹H NMR (250 MHz, d⁶DMSO) δ(ppm): 8.12–7.95 (m, 4H), 7.60–7.45 (m, 3H), 2.44 (s, 3H), 2.35 (s, 3H)

DESCRIPTION 16
2'-Methyl-4'-(5-methyl-1,3,4-oxadiazol-2-yl)biphenyl-4-carboxylic acid The title compound was prepared from 2-(4-bromo-3-methylphenyl)-5-methyl-1,3,4-oxadiazole (EP 0533268 A1) using a procedure similar to Description 15 (72%).

¹H NMR (250 MHz, CDCl₃+d⁶DMSO) δ(ppm): 8.02 (d, 2H), 7.86 (s, 1H), 7.80 (brd, 1H), 7.32 (d, 2H), 7.27 (d, 1H), 2.54 (s, 3H), 2.26 (s, 3H)

DESCRIPTION 17
3-(2-Dimethylaminoethoxy)aniline

The title compound was prepared in 88% yield from 3-nitrophenol following the procedures outlined in Descriptions 1 and 2.

¹H NMR (200 MHz, CDCl₃) δ(ppm): 7.05 (t, 1H), 6.4–6.24 (m, 3H), 4.04 (t, 2H), 367 (brs, 2H), 2.71 (t, 2H), 2.32 (s, 6H)

DESCRIPTION 18
N,N-Dimethyl-N'-(2-methoxyphenyl)ethylenediamine

2-Anisidine (5.9 ml, 0.05 mole) and 2-dimethylaminoethyl chloride hydrochloride (5.0 g, 0.035 mole) were dissolved in ethanol (75 ml) and treated with sodium carbonate (7.42 g, 0.07 mole). The mixture was heated under reflux for 7 hours. After cooling to room temperature, the reaction mixture was filtered, and the filtrate evaporated in vacuo. The residue was dissolved in H₂O and 10% NaOH solution was added until basic. The mixture was extracted into Et₂O, dried (Na₂SO₄) and evaporated in vacuo to give an orange oil. This was purified by flash column chromatography, eluting with ethyl acetate to afford the title compound as a pale orange oil (3.28 g, 48%).

¹H NMR (250 MHz, CDCl₃) δ(ppm): 6.87 (dt, 1H), 6.75 (dd, 1H), 6.68 (dd, 1H), 6.60 (dd, 1H), 4.62 (brs, 1H), 3.82 (s, 3H), 3.15 (m, 2H), 2.58 (t, 2H), 2.25 (s, 6H)

DESCRIPTION 19
N,N-Dimethyl-N'-(2-methoxy-5-nitrophenyl)ethylenediamine

N,N-dimethyl-N'-(2-methoxyphenyl)ethylenediamine (D18, 1.5 g, 0.0077 mole) was dissolved in 5N sulphuric acid (0.86 ml) and the water was removed in vacuo. Conc. H₂SO₄ (6.5 ml) was added and the mixture stirred until homogeneous, then cooled to 0° C. Potassium nitrate (1.01 g, 0.01 mole) was added portionwise, maintaining the temperature below 10° C., and the mixture was stirred at room temperature for 4 hours. The reaction mixture was poured onto ice (150 ml) and made slightly alkaline by addition of sodium carbonate. This solution was extracted into EtOAc, dried (Na₂SO₄) and evaporated in vacuo, to leave an orange oil. This was purified by flash column chromatography to afford the title compound as an orange oil (0.90 g, 49%)

¹H NMR (250 MHz, CDCl₃) δ(ppm): 7.62 (dd, 1H), 7.36 (d, 1H), 6.75 (d, 1H), 4.95 (brs, 1H), 3.94 (s, 3H), 3.23 (q, 2H), 2.63 (t, 2H), 2.29 (s, 6H)

DESCRIPTION 20
N,N-Dimethyl-N'-t-butyloxycarbonyl-N'-(2-methoxy-5-nitrophenyl)-ethylenediamine N,N-Dimethyl-N'-(2-methoxy-5-nitrophenyl)ethylenediamine (D19, 0.90 g, 0.0038 mole) in dichloromethane (50 ml) was treated with triethylamine (0.58 ml, 0.42 g) and di-t-butyldicarbonate (1.0 g, 0.0046 mole) and stirred for 24 hours at room temperature. The reaction mixture was washed with H₂O, dried (Na₂SO₄) and evaporated in vacuo to give the title compound as an orange oil (0.50 g, 39%)

¹H NMR (250 MHz, CDCl₃) δ(ppm): 8.28–8.10 (m, 2H), 6.98 (d, 1H), 3.96 (s, 3H), 3.72–3.28 (brs, 2H), 2.45 (t, 2H), 2.24 (s, 6H), 1.54 (brs, 2H), 1.35 (brs, 7H)

DESCRIPTION 21
N,N-Dimethyl-N'-t-butyloxycarbonyl-N'-(5-amino-2-methoxyphenyl)ethylenediamine The title compound was prepared from N,N-dimethyl-N'-t-butyloxycarbonyl-N'-(2-methoxy-5-nitrophenyl) ethylenediamine (D20, 0.50 g, 0.0015 mol) using the method of Description 2 (0.37 g, 80%).

$^1$H NMR (250 MHz, CDCl$_3$) δ(ppm): 6.65 (d, 1H), 6.50 (d, 2H), 3.68 (s, 3H), 3.60–3.02(m, 4H), 2.49 (t, 2H), 2.16 (s, 6H), 1.45 (brs, 2H), 1.28 (brs, 7H)

DESCRIPTION 22
N-[3-[N-(2-Dimethylaminoethyl)-N-t-butyloxycarbonylamino]-4-methoxyphenyl]-2'-methyl-4'-(5-methyl-1,2,4-oxadiazol-3-yl)biphenyl-4-carboxamide The title compound was prepared from N,N-dimethyl-N'-t-butyloxycarbonyl-N'-(5-amino-2-methoxyphenyl) ethylenediamine (D21, 0.37 g, 0.0012 mole) and 2'-methyl-4'-(5-methyl-1,2,4-oxadiazol-3-yl) biphenyl-4-carboxylic acid (EP 0533268 A1) (0.34 g, 0.0012 mol) using the method of Example 1 (0.40 g, 57%)

$^1$H NMR (250 MHz, CDCl$_3$) δ(ppm): 8.10–7.83 (m, 4H), 7.83–7.61 (m, 1H), 7.53–7.20 (m, 4H), 6.97–6.62 (m, 1H), 3.82 (s, 2H), 3.51 (brs, 4H), 2.70 (s, 3H), 2.62–2.41 (m,2H), 2.41–2.11 (m, 9H), 1.58 (s, 5H), 1.35 (s, 4H)

DESCRIPTION 23
3-(3-Dimethylaminopropoxy)-4-methoxyaniline

The title compound was prepared from 2-methoxy-5-nitrophenol and 3-dimethyaminopropyl chloride hydrochloride using a similar procedure to Descriptions 1 and 2 (58%).

$^1$H NMR (250 MHz, CDCl$_3$ δ(ppm): 6.72 (d, 1H), 6.35 (d, 1H), 6.23 (dd, 1H), 4.02 (t, 2H), 3.80 (s, 3H), 3.62–3.07 (brs, 2H), 2.46 (t, 2H), 2.26 (s, 6H), 2.12–1.92 (m, 2H)

DESCRIPTION 24
N-[3-(2-Dimethylaminoethoxy)-4-methoxyphenyl]-4'-methoxycarbonyl-2'-methylbiphenyl-4-carboxamide The title compound was prepared from 4'-methoxycarbonyl-2'-methylbiphenyl-4-carboxylic acid (D14) and 2-(dimethylaminoethoxy)-4-methoxyaniline (D2) using a similar procedure to Example 1, as a white solid (13%) mp 131°–133° C.

$^1$H NMR (250 MHz, CDCl$_3$) δ(ppm): 8.3 (brs, 1H), 8.03–7.87 (m, 4H), 7.51 (d, 1H), 7.40 (d, 2H), 7.28 (d, 1H), 7.11 (dd, 1H), 6.84 (d, 1H), 4.12 (t, 2H), 3.94 (s, 3H), 3.84 (s,3H), 2.78 (t, 2H), 2.30 (s, 9H).

DESCRIPTION 25
N,N-Dimethyl-3-(5-amino-2-methoxyphenyl)acrylamide

4-Amino-2-bromoanisole (1.70 g, 8.42 mmol), tri-o-tolylphosphine (0.205 g, 0.672 mmol), N,N-dimethylacrylamide (0.950 ml, 9.26 mmol), triethylamine (2.92 ml, 21.05 mmol), palladium (II) acetate (0.038 g, 0.168 mmol) and dry DMF (4 ml) were heated together with stirring under argon at 110° C. After 4 h, the reaction mixture was allowed to cool and was partitioned between ethyl acetate and water. The aqueous layer was then extracted with ethyl acetate (1×). The combined organic layers were then dried (Na$_2$SO$_4$) and evaporated under reduced pressure to give an orange oil which was dried in vacuo (1.3 g). The oil was purified by SiO$_2$ chromatography (EtOAc→10% MeOH/EtOAc as eluant) to give the title compound as a yellow solid (0.362 g, 20%)

$^1$H NMR (200 MHz, CDCl$_3$) δ(ppm): 7.83 (d, 1H), 6.95 (d, 1H), 6.87 (d, 1H), 6.75 (d, 1H), 6.68 (dd, 1H), 3.80 (s, 3H), 3.48 (s, 2H), 3.18 (s, 3H), 3.05 (s, 3

DESCRIPTION 26
N,N-Dimethyl-3-(5-amino-2-methoxyphenyl)propylamine

The product from description 25 (0.220 g, 1.00 mmol) was dissolved in ethanol (30 ml) and hydrogenated at atmospheric pressure. After 4 h, the reaction mixture was filtered through Kieselguhr. The filter pad was then washed with ethanol and the filtrate evaporated under reduced pressure to give a brown oil which was dried in vacuo (0.213 g). The oil was then dissolved in dry THF (1.5 ml) and treated with lithium aluminium hydride (0.052 g, 1.372 mmol) with stirring under argon. The reaction mixture was then heated to reflux. After 4 h, the reaction mixture was allowed to cool and was treated with water (0.052 ml), 10% NaOH (0.078 ml) and water (0.130 ml). The reaction mixture was then stirred for a further ½ h, before being filtered. The filter pad was then washed with TBF (2×10 ml) and the filtrate was evaporated under reduced pressure to give the title compound as a brown oil which was dried in vacuo (0.152 g, 80%).

$^1$H NMR (250 MHz, CDCl$_3$) δ(ppm): 6.69 (d, 1H), 6.52 (m, 2H), 3.75 (s, 3H), 3.40 (s, 2H), 2.53 (t, 2H), 2.30 (t, 2H), 2.20 (s, 6H), 1.75 (m, 2H).

DESCRIPTION 27
E-N,N-Dimethyl-3-(5-amino-2-methoxyphenyl)prop-2-enylamine A slurry of lithium aluminium hydride (0.065 g, 1.72 mmol) in dry TBHF (10 ml) under argon was treated with c. H$_2$SO$_4$ (0.048 ml, 0.860 mmol) with stirring. After 1 h, a solution of the product from description 25 (0.126 g, 0.573 mmol) in dry THF (5 ml) was added and the mixture was heated to reflux. After 2.5 h, the reaction mixture was allowed to cool and the resulting yellow suspension was then treated with 40% NaOH (0.147 ml), followed by water (0.074 ml). The mixture was then stirred at room temperature for ½ h before being filtered through Kieselguhr. The filter pad was then washed with TBF (2×5 ml) and the filtrate was evaporated under reduced pressure and dried in vacuo to give the title compound as a yellow oil (0.090 g, 76%).

$^1$H NMR (200 MHz, CDCl$_3$) δ(ppm): 6.78 (s, 1H), 6.64 (d, 2H), 6.50 (dd, 1H), 6.12 (m, 1H), 3.70 (s, 3H), 3.30 (s, 2H), 3.00 (d, 2H), 2.21 (s, 6H).

DESCRIPTION 28
N,N-Dimethyl-3-(4-nitrophenoxy)propylamine

A stirred solution of diethyl azodicarboxylate (4.6 ml, 0.029 mole) and triphenylphosphine (7.60 g, 0.029 mole) in dry TBF (100 ml) was cooled to 0° C. 3-(Dimethylamino) propanol (3.43 ml, 0.029 mole) was added, followed by 4-nitrophenol (4.0 g, 0.029 mole) and the reaction mixture was stirred for 18 h at room temperature. The solvent was removed in vacuo, and the residue partitioned between 5N HCl and ethyl acetate. The aqueous layer was basified with 10% NaOH solution and extracted into ethyl acetate, dried (MgSO$_4$) and evaporated in vacuo to leave the title compound as a yellow oil (3.2 g, 50%).

$^1$H NMR (250 MHz, CDCl$_3$) δ(ppm): 8.19 (d, 2H), 6.97 (d, 2H), 4.13 (t, 2H), 3.58 (br 2H), 2.28 (s, 6H), 2.01 (quintet, 2H).

DESCRIPTION 29
4-(3-Dimethylaminopropoxy)aniline

The title compound was prepared from N,N-dimethyl-3-(4-nitrophenoxy)propylamine (D28) using a similar procedure to Description 2, as an orange oil (77%).

$^1$H NMR (250 MHz, CDCl$_3$) δ(ppm): 6.73 (d, 2H), 6.62 (d, 2H), 3.93 (t, 2H), 3.53 (br s, 2H), 2.46 (t, 6H), 1.93 (quintet, 2H).

DESCRIPTION 30
2-(2-Pyrrolidin-1-ylethoxy)-4-nitroanisole

A stirred solution of 2-methoxy-5-nitrophenol (1.5 g, 0.0088 mole), 1-pyrrolidineethanol (1.03 ml, 0.0088 mole) and triphenylphosphine (2.4 g, 0.0088 mole) in THF (50 ml) at room temperature under argon was treated with diethyl azodicarboxylate (1.4 ml, 0.0088 mole). The reaction mixture was stirred for 1 h, then concentrated in vacuo and the residue treated with 2M HCl acid (50 ml) and ethyl acetate (50 ml). The mixture was shaken well, then the acid layer separated, washed with ethyl acetate (2×30 ml) and then basified by addition of potassium carbonate. The basic mixture was extracted with ethyl acetate (2×50 ml) and the combined extract dried ($Na_2SO_4$) and concentrated in vacuo to afford the title compound as a yellow oil (1.43 g, 61%).

$^1$H NMR (250 MHz, $CDCl_3$) δ(ppm): 7.92 (dd, 1H), 7.79 (d, 1H), 6.92 (d, 1H), 4.23 (t, 2H), 3.96 (s, 3H), 2.99 (t, 2H), 2.72–2.60 (m, 4H).

DESCRIPTION 31
3-(2-Pyrrolidin-1-ylethoxy)-4-methoxyaniline

The title compound was prepared from 2-(2-pyrrolidin-1-ylethoxy)-4-nitroanisole (D30) using a similar procedure to Description 2 (96%).

$^1$H NMR (250 MHz, $CDCl_3$) δ(ppm): 6.70 (d, 1H), 6.32 (d, 1H), 6.22 (dd, 1H), 4.10 (t, 2H), 3.78 (s, 3H), 3.50 (br s, 2H), 2.93 (t, 2H), 2.70–2.55 (m, 4H), 1.90–1.70 (m, 4H).

DESCRIPTION 32
4-Bromo-3-methylbenzamide oxime

Methanol (20 ml) at 5° C. was treated portionwise over 5 min. with stirring with potassium t-butoxide (1.68 g, 0.015 mole), then after a further 5 mins the solution was treated with hydroxylamine hydrochloride (1.11 g, 0.016 mole). The resulting mixture was allowed to warm to room temperature, stirred for 1 h, then treated with a solution of 4-bromo-3-methylbenzonitrile (2.0 g, 0.010 mole) in methanol (10 ml) and heated under reflux for 3 h. The mixture was allowed to cool, then filtered through kieselguhr and the filtrate concentrated in vacuo to afford the title compound as a white solid (2.56 g, 100%).

$^1$H NMR (250 MHz, $d^6$DMSO) δ(ppm): 7.67 (d, 1H), 7.56 (d, 1H), 7.42 (dd, 1H), 5.85 (br s, 2H), 2.35 (s, 3H).

DESCRIPTION 33
2-(4-Bromo-3-methylphenyl)-5-ethyl-1,2,4-oxadiazole

A stirred suspension of 4-bromo-3-methylbenzamide oxime (D32, 400 mg, 0.0017 mole) in toluene (20 ml) was treated with propionic anhydride (0.64 ml, 0.0050 mole) and the mixture heated under reflux for 4 h. The reaction mixture was allowed to cool, then treated with 10% $Na_2CO_3$ solution (30 ml), stirred well for 1 h and then extracted with ethyl acetate (2×40 ml). The combined extract was dried ($Na_2SO_4$), concentrated in vacuo and the residue chromatographed on silica gel eluting with 30% ether/60–80 petrol to afford the title compound as a pale yellow oil (430 mg, 95%).

$^1$H NMR (250 MHz, $CDCl_3$) δ(ppm): 7.95 (d, 1H), 7.75 (dd, 1H), 7.63 (d, 1H), 2.98 (q, 2H), 2.48 (s, 3H), 1.45 (t, 3H)

DESCRIPTION 34
2'-Methyl-4'-(5-ethyl-1,2,4-oxadiazol-3-yl)biphenyl-4-carboxylic acid The title compound was prepared from 2-(4-bromo-3-methylphenyl)-5-ethyl-1,2,4-oxadiazole (D33) using a procedure similar to Description 15 (85%).

$^1$H NMR (250 MHz, $CDCl_3$+$d^6$DMSO) δ(ppm): 8.02 (d, 2H), 7.90 (s, 1H), 7.85 (d, 1H), 2.91 (q, 2H), 2.25 (s, 3H), 1.38 (t, 3H).

DESCRIPTION 35
2-(4-Bromo-3-methylphenyl)-5-(dimethylamino)-1,2,4-oxadiazole 4-Bromo-3-methylbenzamide oxime (D32, 1.5 g, 0.0065 mole) was added portionwise over 10 min with stirring to trichloroacetic anhydride (18 ml) at 10° C. under argon. The reaction mixture was allowed to warm up to room temperature and stir for 4 h, then added slowly to a well stirred mixture of excess aqueous sodium bicarbonate solution and ethyl acetate at ice bath temperature. When effervescence had ceased, the ethyl acetate layer was separated, dried ($Na_2SO_4$) and concentrated in vacuo to leave the 5-trichloromethyloxadiazole as a pale yellow solid. This was treated with a 33% solution of dimethylamine in IMS (25 ml) and heated under reflux for 18 h, then concentrated in vacuo. The residue was treated with 10% $Na_2CO_3$ solution (20 ml) and extracted with ethyl acetate (2×30 ml). The combined extract was dried ($Na_2SO_4$), concentrated in vacuo and the residue chromatographed on silica gel eluting with 1:1 ether/60–80 petrol to afford the title compound as a white solid (1.14 g, 62%).

$^1$H NMR (250 MHz, $CDCl_3$) δ(ppm): 7.88 (d, 1H), 7.69 (dd, 1H), 7.58 (d, 1H), 3.20 (s, 6H), 2.44 (s, 3H).

DESCRIPTION 36
2'-Methyl-4'-(5-dimethylamino-1,2,4-oxadiazol-3-yl)biphenyl-4-carboxylic acid The title compound was prepared from 2-(4-bromo-3-methylphenyl)-5-(dimethylamino)-1,2,4-oxadiazole (D35) using a similar procedure to Description 15 (64%) as a white solid.

$^1$H NMR (250 MHz, $d^6$DMSO) δ(ppm): 13.1 (br s, 1H), 8.03 (d, 2H), 7.85 (s, 1H), 7.80 (d, 1H), 7.52 (d, 2H), 7.37 (d, 1H), 3.15 (s, 6H), 2.30 (s, 3H).

DESCRIPTION 37
4-Bromo-3-methyl benzamide

4-Bromo-3-methylbenzoic acid (19 g, 0.088 mole) was dissolved in dichloromethane (200 ml) and treated with oxalyl chloride (12 ml, 0.013 mole), followed by DMF (3 drops). The reaction mixture was stirred for 18 h at room temperature, after which the solvent was removed in vacuo. The acid chloride was added dropwise to 0.88 ammonia solution (250 ml) with stirring. The resulting solid was filtered off, washed with ether and dried to afford the title compound (18.03 g, 96%).

$^1$H NMR (200 MHz, $d^6$DMSO) δ(ppm): 8.02 (s, 1H), 7.88 (s, 1H), 7.69–7.61 (m, 2H), 7.44 (s, 1H), 2.40 (s, 3H)

DESCRIPTION 38
4-Bromo-3-methylthiobenzamide

4-Bromo-3-methylbenzamide (D37, 1.0 g, 0.0047 mole) was dissolved in THF (50 ml), treated with Lawessons reagent (0.95 g, 0.0024 mole) and stirred under argon for 4 h. The solvent was removed in vacuo and the residue purified by flash chromatography on silica gel eluting with 10% EtOH/$CHCl_3$ to afford the title compound as a yellow solid (0.87 g, 80%).

$^1$H NMR (200 MHz, $CDCl_3$) δ(ppm): 7.78 (s, 1H), 7.72 (br s, 1H), 7.63–7.45 (m, 2H), 7.19 (br s, 1H), 2.45 (s, 3H).

DESCRIPTION 39
2-(4-Bromo-3-methylphenyl)-4-methylthiazole

4-Bromo-3-methylthiobenzamide (D38, 0.87 g, 0.0038 mole) was dissolved in ethanol (60 ml) and treated with chloroacetone (0.39 ml, 0.0049 mole). The reaction mixture was heated under reflux for 5 h, then more chloroacetone (0.39 ml, 0.0049 mole) was added and the mixture heated under reflux for a further 3 h. After cooling to room temperature, the solvent was removed in vacuo to leave the title compound as a pale oil (1.00 g, 98%).

$^1$H NMR (200 MHz; CDCl$_3$) δ(ppm): 8.20 (d, 1H), 7.95 (dd, 1H), 7.69 (d, 1H), 7.22 (s, 1H), 2.76 (s, 3H), 2.50 (s, 3H).

DESCRIPTION 40
2'-Methyl-4'-(4-methylthiazol-2-yl)biphenyl-4-carboxylic acid The title compound was prepared from 2-(4-bromo-3-methylphenyl)-4-methylthiazole (D39, 1.00 g, 0.0037 mole) using the method of Description 15 (0.77 g, 67%).

$^1$H NMR (200 MHz, d$^6$DMSO) δ(ppm): 8.03 (d, 2H), 7.89 (s, 1H), 7.82 (dd, 1H), 7.52 (d, 2H), 7.40–7.22 (m, 2H), 2.46 (s, 3H), 2.32 (s, 3H).

DESCRIPTION 41
N-Methoxy-N-methyl-4-bromo-3-methylbenzamide

A stirred suspension of 4-bromo-3-methylbenzoic acid (5.0 g, 0.023 mole) in thionyl chloride (20 ml) was heated under reflux for 2 h, then concentrated in vacuo to leave the acid chloride as a pale yellow solid. This was dissolved in dichloromethane (100 ml) and added dropwise over 10 minutes to a stirred suspension of N,O-dimethylhydroxylamine hydrochloride (2.4 g, 0.025 mole) and pyridine (5.6 ml, 0.069 mole) in dichloromethane (150 ml) and acetonitrile (20 ml) at –20° C. The mixture was allowed to warm to room temp. over 3 h, then treated with 10% Na$_2$CO$_3$ solution (100 ml) and extracted with dichloromethane (2×200 ml). The combined extract was dried (Na$_2$SO$_4$) and concentrated in vacuo to afford the title compound as a pale yellow oil (5.9 g, 100%)

$^1$H NMR (200 MHz, CDCl$_3$) δ(ppm): 7.60–7.50 (m, 2H), 7.36 (dd, 1H), 3.55 (s, 3H), 3.35 (s, 3H), 2.42 (s, 3H).

DESCRIPTION 42
(4-Bromo-3-methylbenzoyl)methyl phenyl sulphone

A stirred solution of diisopropylamine (3.6 ml, 0.026 mole) in dry THF (60 ml) at –60° C. under argon was treated with 1.5M methyllithium in ether (15.3 ml, 0.023 mole). After 15 minutes, the solution was treated dropwise over 5 minutes with a solution of methyl phenyl sulphone (2.8 g, 0.020 mole) in dry THF (20 ml). The mixture was kept at –60° C. for a further 10 minutes, then treated with a solution of N-methoxy-N-methyl-4-bromo-3-methylbenzamide (D41, 4.4 g, 0.017 mole) in dry THF (30 ml) and allowed to warm to room temp. over 1.5 h. The reaction mixture was treated with 10% Na$_2$CO$_3$ solution (70 ml), then concentrated in vacuo to approx. 100 ml volume and extracted with ethyl acetate (2×100 ml). The combined extract was dried and concentrated in vacuo to afford the title compound as a pale orange solid (6.0 g, 100%).

$^1$H NMR (250 MHz, CDCl$_3$) δ(ppm): 7.78–7.46 (m, 8H), 4.51 (d, 1H), 4.30 (d, 1H), 2.43 (s, 3H).

DESCRIPTION 43
(4-Bromo-3-methylphenyl)pyrazine

A stirred solution of (4-bromo-3-methylbenzoyl)methyl phenyl sulphone (D42, 1.5 g, 0.0044 mole) in dichloromethane (30 ml) at 0° C. under argon was treated with trifluoroacetic acid (0.70 ml, 0.005 mole) followed by trifluoroacetic anhydride (0.77 ml, 0.010 mole). After 30 minutes the solution was concentrated in vacuo, and the residue treated with a solution of sodium hydrogen carbonate (1.47 g, 0.017 mole) in water (30 ml), followed by ethanol (50 ml) and dichloromethane (50 ml). After 30 minutes, the two phase system was treated with ethylenediamine (0.33 ml, 0.005 mole) and stirred well at room temp. for 18 h, then the dichloromethane layer was separated, dried and concentrated in vacuo. The residue was dissolved in ethanol (30 ml) treated with potassium hydroxide (0.28 g, 0.005 mole) and heated under reflux for 6 h, then concentrated under vacuum and the residue treated with water (30 ml) and extracted with dichloromethane (2×50 ml). The combined extract was dried (Na$_2$SO$_4$), concentrated in vacuo and the residue chromatographed on silica gel eluting with 25–40% ether/60–80 petrol to afford the title compound as a yellow solid (300 mg, 27%).

$^1$H NMR (250 MHz, CDCl$_3$) δ(ppm): 9.00 (d, 1H), 8.62 (m, 1H), 8.52 (d, 1H), 7.90 (s, 1H), 7.68 (s, 2H)

DESCRIPTION 44
2'-Methyl-4'-pyrazinylbiphenyl-4-carboxylic acid

The title compound was prepared from (4-bromo-3-methylphenyl)pyrazine (D43) using a similar procedure to Description 15 as a yellow solid (100%).

$^1$H NMR (250 MHz, CDCl$_3$+d$^6$DMSO) δ(ppm): 9.09 (d, 1H), 8.67 (m, 1H), 8.54 (d, 1H), 8.12 (d, 2H), 7.98 (s, 1H), 7.91 (dd, 1H), 7.45 (d, 2H), 7.39 (d, 1H), 2.38 (s, 3H).

DESCRIPTION 45
Ethyl 2-methoxy-5-nitrophenylxanthate

A solution of 2-methoxy-5-nitroaniline (16.8 g) in concentrated hydrochloric acid (60 ml) was cooled to 0° C., and treated portionwise with sodium nitrite (7.4 g), in water (40 ml), maintaining the temperature between 0°–5° C. The resulting ice-cold diazonium salt solution was added portionwise to a solution of ethyl potassium xanthate (18.66 g) in water (80 ml) at 45° C. and this temperature was maintained throughout, and for 1 hh after addition. The cooled reaction mixture was extracted with ether, and the organic phase washed with 10% (aq) sodium hydroxide, then water. The dried (Na$_2$SO$_4$) organic phase was evaporated under reduced pressure to leave the title compound as a red oil which was purified by column chromatography on silica gel, eluting with 1:1 ether: 60°–80° petroleum-ether (4.71 g, 23%).

$^1$H NMR (200 MHz, CDCl$_3$) δ(ppm): 8.45–8.3 (m, 2H), 7.05 (d, 1H), 4.61 (q, 2H), 3.99 (s, 3H), 1.34 (t, 3H).

DESCRIPTION 46
2-Methoxy-5-nitrobenzenethiol

A solution of ethyl 2-methoxy-5-nitrophenylxanthate (D45) (1.78 g) in ethanol (40 ml) was treated with solid potassium hydroxide (913 mg) and the mixture stirred at room temperature under argon for ¼ h. The solvent was evaporated under reduced pressure and the residue acidified with 5N hydrochloric acid and extracted into ethyl acetate. The organic phase was dried (Na$_2$SO$_4$) and the solvent evaporated under reduced pressure to give the title compound as a yellow solid (1.13 g, 94%).

$^1$H NMR (250 MHz, CDCl$_3$) δ(ppm): 8.19 (s, 1H), 8.05 (d, 1H), 6.19 (d, 1H), 4.02 (m, 4H)

DESCRIPTION 47
2-(2-Dimethylamninoethylthio)-4-nitroanisole

A solution of 2-methoxy-5-nitrobenzenethiol (D46) (1.13 g) in dimethylsulphoxide (50 ml) was treated with potassium carbonate (5 g) and N,N-dimethylaminoethyl chloride (5 ml) and the mixture stirred under argon for 0.5 h. The reaction mixture was filtered and the solvent evaporated under reduced pressure to leave a yellow oil, which was partitioned between water and diethyl ether. The dried (Na$_2$SO$_4$) organic phase was evaporated under reduced pressure and the residue saturated with 1:2 ether: 60°–80° petroleum-ether. The mixture was filtered and the filtrate evaporated under reduced pressure to give the title compound as a yellow oil (868 mg, 56%)

¹H NMR (200 MHz, CDCl₃) δ(ppm): 8.12–8.00 (m, 2H), 6.89 (d, 1H), 4.0 (s, 3H), 3.10 (t, 2H), 2.66 (t, 2H), 2.32 (s, 6H)

DESCRIPTION 48
4-Amino-2-(2-dimethylaminoethylthio)anisole

The title compound was prepared from 2-(2-dimethylaminoethylthio)-4-nitroanisole (D47) (788 mg) using a similar procedure to Description 2 (88%).

¹H NMR (200 MHz, CDCl₃) δ(ppm): 6.72–6.62 (m, 2H), 6.51 (d, 1H), 3.82 (s,3H), 3.45 (brs, 2H), 3.05–2.9 (m, 2H), 2.61–2.5 (m, 2H), 2.26 (s, 6H).

DESCRIPTION 49
3-(2-Dimethylaminoethoxy)-4-iodoacetanilide

Following the procedure outlined in Description 1 (except that dimethoxyethane was used in place of acetone/water) 5-acetamido-2-iodophenol (prepared as described by H. Wunderer, Arch. Pharmaz. 306 371 (1973)) (1 g) was converted to the title compound (1.1. g, 88%).

¹H NMR (200 MHz, CDCl₃) δ(ppm): 7.64 (d, 1H), 7.4–7.31 (m, 2H), 6.69 (d, 1H), 4.11 (t, 2H), 2.81 (t, 2H), 2.37 (s, 6H), 2.17 (s, 3H).

DESCRIPTION 50
3-(2-Dimethylaminoethoxy)-4-iodoaniline

A solution of 3-(2-dimethylaminoethoxy)-4-iodoacetanilide (D49) (1.02 g) in ethanol (25 ml) was treated with 10% potassium hydroxide solution (25 ml). The mixture was heated under reflux for 3 h, and the solvent was evaporated under reduced pressure and the residue diluted with water and extracted with chloroform. The organic phase was dried (Na₂SO₄) and evaporated under reduced pressure to leave the title compound (0.76 g, 83%)

¹H NMR (200 MHz, CDCl₃) δ(ppm): 7.44 (d, 1H), 6.2 (s, 1H), 6.11 (d, 1H), 4.05 (t, 2H), 3.71 (brs, 2H), 2.8 (t, 2H), 2.38 (s, 6H).

DESCRIPTION 51
2-Ethyl-5-nitrophenol

A solution of 2-ethyl-5-nitroaniline (prepared as described by E. Dyszer et al, Przemysl. Chem 42 (8) 433–5 (1963)) (5 g) in concentrated sulphuric acid (27 ml) and water (160 ml) at 0° C., was treated with sodium nitrite (2.3 g) in water (5 ml) over 5 minutes with stirring. After ¼ h at 0° C., urea (2 g) was added and the mixture heated to 80° C. for 2 h. After stirring overnight at room temperature, the pH was adjusted to pH 10–12 with 10% sodium hydroxide, and the mixture extracted into ethyl acetate. The organic phase was dried (Na₂SO₄) and the solvent evaporated under reduced pressure. Flash column chromatography on silica gel, eluting with ethyl acetate and 60°–80° C. petroleum-ether gave the title compound (2.91 g, 58%).

¹H NMR (250 MHz, CDCl₃) δ(ppm): 7.78 (d, 1H), 7.65 (s, 1H), 7.29 (d, 1H), 5.7 (s, 1H), 2.72 (q, 2H), 1.27 (t, 3H)

DESCRIPTION 52
3-(2-Dimethylaminoethoxy)-4-ethylnitrobenzene

The title compound was prepared from 2-ethyl-5-nitrophenol (D51) using a similar procedure to Description 49 as an orange oil (78%)

¹H NMR (250 MHz, CDCl₃) δ(ppm): 7.8 (d, 1H), 7.69 (s, 1H), 7.28 (d, 1H), 4.17 (t, 2H), 2.82 (t, 2H), 7.72 (q, 2H), 2.40 (s, 6H), 1.25 (t, 3H)

DESCRIPTION 53
3-(2-Dimethylaminoethoxy)-4-ethylaniline

The title compound was prepared from 3-(2-diethylaminoethoxy)-4-ethylnitrobenzene (D52) using a similar procedure to Description 2 as a pale yellow oil (89%)

¹H NMR (200 MHz, CDCl₃) δ(ppm): 6.91 (d, 1H), 6.3–6.2 (m, 2H), 4.04 (t, 2H), 3.45 (brs, 2H), 2.77 (t, 2H), 2.54 (q, 2H), 2.36 (s, 6H), 1.14 (t, 3H)

DESCRIPTION 54
2-Isopropyl-5-nitrophenol

The title compound was prepared from 2-isopropyl-5-nitroaniline (prepared using a similar procedure to that described by E. Dyszer et al., Przemysl. Chem. 42 (8) 433–5 (1963)), according to the method outlined in Description 51, as a dark brown oil (82%).

¹H NMR (200 MHz, CDCl₃) δ(ppm): 7.8 (d, 1H), 7.62 (s, 1H), 7.32 (d, 1H), 3.4–3.2 (m, 1H), 1.3 (s, 3H), 1.26 (s, 3H).

DESCRIPTION 55
3-(2-Dimethylamninoethoxy)-4-isopropylnitrobenzene

The title compound was prepared from 2-isopropyl-5-nitrophenol (D54) using a similar procedure to Description 49 (37%).

¹H NMR (200 MHz, CDCl₃) δ(ppm): 7.82 (d, 1H), 7.68 (s, 1H), 7.32 (d, 1H), 4.16 (t, 2H), 3.5–3.3 (m, 1H), 2.81 (t, 2H), 2.39 (s, 6H), 1.35–1.11 (m, 6H)

DESCRIPTION 56
3-(2-Dimethylaminoethoxy)-4-isopropylaniline

The title compound was prepared from 3-(2-imethylaminoethoxy)-4-isopropylnitrobenzene (D55) using a similar procedure to Description 2 (98%)

¹H NMR (200 MHz, CDCl₃) δ(ppm): 6.98 (d, 1H), 6.3–6.2 (m, 2H), 4.02 (t, 2H), 3.55 (brs, 2H), 3.33–3.11 (m,1H), 2.75 (t, 2.35 (s, 6H), 1.19 (s,3H), 1.15 (s, 3H).

DESCRIPTION 57
3-(2-Dimethylaniinoethoxy)-4-chloronitrobenzene

The target compound was prepared from 2-chloro-5-nitrophenol (prepared as described by J. B. S. Bonilha et al, Tetrahedron 49 (15) 3053 (1993)) using a similar procedure to Description 1, in which 1,2-dimethoxyethane was used in place of acetone and water. (70%)

¹H NMR (200 MHz, CDCl₃) δ(ppm): 7.85–7.76 (m, 2H), 7.51 (d, 1H), 4.12 (t, 2H), 2.85 (t, 2H), 2.40 (s, 6H)

DESCRIPTION 58
3-(2-Dimethylaminoethoxy)-4-chloroaniline

A solution of 3-(2dimethylaminoethoxy)-4chloronitrobenzene (D57) (295 mg) in ethanol (5 ml) was heated to 60° C. and treated dropwise with a solution of stannous chloride (0.82 g) in concentrated hydrochloric acid (1.5 ml) with stiring. After heating to reflux for ½ h, the reaction mixture was cooled, diluted with water and basified with 40% NaOH, then extracted into dichloromethane. The dried (Na₂SO₄) organic phase was evaporated under reduced pressure to give the title compound as a yellow oil. (221 mg, 85%).

¹H NMR (200 MHz, CDCl₃) δ(ppm): 7.1 (d, 1H), 6.28 (s, 1H), 6.2 (d, 1H), 4.05 (t, 2H), 3.68 (br s, 2H), 2.78 (t, 2H), 2.35 (s, 6H).

DESCRIPTION 59
3-(2-Dimethylaminoethoxy)-4-bromonitrobenzene

The target compound was prepared from 2-bromo-5-nitrophenol (prepared as described by J. B. S. Bonilha et al, Tetrahedron 49 (15) 3053 (1993)) using a similar procedure to Description 1, in which 1,2-dimethoxyethane was used in place of acetone and water (56%).

$^1$H NMR (200 MHz, CDCl$_3$) δ(ppm): 7.77–7.69 (m, 3H), 4.22 (t, 2H), 2.85 (t, 2H), 2.4 (s, 6H).

DESCRIPTION 60
3-(2-Dimethylaminoethoxy)-4-bromoaniline

The title compound was prepared from 3-(2-dimethylaminoethoxy)-4-bromonitrobenzene (D59) using a similar method to Description 58. (10%)

$^1$H NMR (200 MHz, CDCl$_3$) δ(ppm): 7.24 (d, 1H), 6.25 (s, 1H), 6.19 (d, 1H), 4.06 (t, 2H), 3.7 (br s, 2H), 2.79 (t, 2H), 2.36 (s, 6H).

DESCRIPTION 61
1-(3-Methyl-4-nitrophenyl)-1,2,4-triazole

A mixture of 4-fluoro-2-methylnitrobenzene (2 g), 1,2,4-triazole (0.9 g) and anhydrous potassium carbamate (1.78 g) was stirred and heated in dimethylsulphoxide (50 ml) at 90° C. for 24 hours. The reaction mixture was cooled, poured into water (200 ml) and extracted with ethyl acetate. The ethyl acetate layer was separated, dried (MgSO$_4$) and evaporated to give an orange solid which was purified by chromatography on silica using pentane/ethyl acetate as eluant, (1.8 g, 69%).

$^1$H NMR (250 MHz, CDCl$_3$) δ(ppm): 8.68 (s, 1H), 8.1–8.3 (m, 2H), 7.65–7.8 (m, 2H), 2.72 (s, 3H).

DESCRIPTION 62
4-(1,2,4-Triazol-1-yl)-2-methylaniline

A mixture of 1-(3-methyl-4-nitrophenyl)-1,2,4-triazole (D61, 1.0 g), 10% Pd/C (200 mg) in ethanol (50 ml) was hydrogenated at ambient temperature and pressure for 5 hours. The reaction mixture was filtered through kieselguhr and the filtrate evaporated to leave the title compound (0.85 g, 98%) which was used directly in the next stage.

DESCRIPTION 63
1-(4-Bromo-3-methylphenyl)-1,2,4-triazole 4-(1,2,4-Triazol-1-yl)-2-methylaniline (D62, 0.55 g) in 48% HBr (10 ml) at −5° C. was stirred while sodium nitrite (0.3 g) was added portionwise over approximately 5 minutes to give a brown sludge which was left for a further 15 minutes. During this time, copper (1) bromide (0.63 g) was heated under reflux in 48% HBr (2 ml) under argon. The brown sludge was added to it portionwise over 5 minutes and the resulting black reaction mixture heated under reflux for a further 1 minute. After cooling slightly, the mixture was poured gently into 10% aqueous ethylenediamine solution to give a purple solution. Ethyl acetate extraction gave the title compound which was purified by chromatography on silica using 4–10% pentane/ethyl acetate as eluant (0.77 g, 73%) Mass spec (CI) MH$^+$238, 240.

DESCRIPTION 64
2'-Methyl-4'-(1,2,4-triazol-1-yl)-1,1'-biphenyl-4-carboxylic acid The title compound (0.15 g) was prepared from 1-(4-bromo-3-methylphenyl)-1,2,4-triazole (D63, 0.2 g) and 4-boronobenzoic acid (0.14 g) as described in Description 15.

DESCRIPTION 65
4'-(5-Methyl-1,2,4-oxadiazol-3-yl)-1,1'-biphenyl-4-carboxylic acid The title compound was prepared from 4-(5-methyl-1,2,4-oxadiazol-3-yl)bromobenzene (0.58 g) and 4-boronobenzoic acid (0.4 g) as described in Description 15 as a white solid (0.64 g, 97%).

$^1$H NMR (250 MHz, d$^6$DMSO) δ(ppm): 12.8–13.3 (br s, 1H), 7.8–8.2 (m, 8H), 2.7 (s, 3H).

DESCRIPTION 66
1-(4-Nitrophenyl)-1,2,4-triazole

The title compound was prepared from 4-fluoronitrobenzene (2 g) and 1,2,4-triazole (1 g) as described in Description 61 to give a white solid (2.6 g, 97%).

$^1$H NMR (250 MHz, CDCl$_3$) δ(ppm): 8.71 (s, 1H), 8.43 (d, 2H), 8.18 (s, 1H), 7.95 (d, 2H).

DESCRIPTION 67
4-(1,2,4-Triazol-1-yl)aniline

The title compound was prepared from 1-(4-nitrophenyl)-1,2,4-triazole (D66, 0.5 g) as described in Description 62, (0.42 g, 85%).

$^1$H NMR (250 MHz, CDCl$_3$) δ(ppm): 8.4 (s, 1H), 7.95 (s, 1H), 7.42 (d, 2H), 6.78 (d, 2H), 3.88 (br s, 2H).

DESCRIPTION 68
1-(4-Bromophenyl)-1,2,4-triazole

The title compound was prepared from 4-(1,2,4-triazol-1-yl)aniline (D67, 0.4 g) as described in Description 63 (0.34 g, 60%).

$^1$H NMR (250 MHz, CDCl$_3$) δ(ppm): 8.58 (s, 1H), 8.12 (s, 1H), 7.58 (d, 2H), 7.48 (d, 2H).

DESCRIPTION 69
4'-(1,2,4-Triazol-1-yl)-1-1'-biphenyl-4-carboxylic acid

The title compound was prepared from 1-(4-bromophenyl)-1,2,4-triazole (D68, 0.34 g) and 4-boronobenzoic acid (0.25 g) as described in Description 15 as a pale yellow crystalline solid (0.37 g, 92%).

Mass spec (EI) M$^+$265 (8%); (CI) MH$^+$266 (100%)

DESCRIPTION 70
2-(4-Nitrophenyl)tetrazole

The title compound was prepared from 4-fluoronitrobenzene (2 g) and tetrazole (1 g) as described in Description 61 as a yellow solid (0.83 g, 31%).

$^1$H NMR (400 MHz, CDCl$_3$) δ(ppm): 8.75 (s, 1H), 8.48 (d, 2H), 8.4 (d, 2H).

DESCRIPTION 71
4-(Tetrazol-2-yl)aniline

The title compound was prepared from 2-(4-nitrophenyl)tetrazole (D70, 0.83 g) as described in Description 62 as white solid (0.79 g, 100%).

$^1$H NMR (250 MHz, CDCl$_3$) δ(ppm): 8.59 (s, 1H), 7.9 (d, 2H), 6.8 (d, 2H), 4.0 (brs, 2H).

DESCRIPTION 72
2-(4-Bromophenyl)tetrazole

The title compound was prepared from 4-(tetrazol-2-yl)aniline (D71, 0.45 g) as described in Description 63 (0.24 g, 38%)

$^1$H NMR (250 MHz, CDCl$_3$) δ(ppm): 8.68 (s, 1H), 8.05 (d, 2H), 7.71 (d, 2H).

DESCRIPTION 73
4'-(Tetrazol-2-yl)-1,1'-biphenyl-4-carboxylic acid

The title compound was prepared from 2-(4-bromophenyl)tetrazole (D72, 0.2 g) and 4-boronobenzoic acid (0.15 g) as described in Description 15 (0.17 g, 72%).

$^1$H NMR (250 MHz, d$^6$DMSO) δ(ppm): 12.9–13.4 (br s, 1H), 9.3 (s, 1H), 8.25 (d, 2H), 8.0–8.15 (m, 4H), 7.9 (d, 2H).

DESCRIPTION 74
4-Borono-3-methylbenzoic acid

A stirred solution of 4-bromo-3-methylbenzoic acid (5.0 g, 0.020 mole) in dry THF (250 ml) at −78° C. under argon was treated with 1.6M n-butyllithium in hexane (36 ml, 0.057 mole). After 15 minutes, the reaction mixture was treated with triisopropylborate (13.4 ml, 0.050 mole), then stirred at −78° C. for 1 h, followed by room temp. for 19 h. The mixture was treated with water (25 ml), then concentrated in vacuo and the residue chromatographed on silica gel eluting with 10% methanol/dichloromethane to afford the title compound as a white solid (2.63 g, 67%).

$^1$H NMR (200 MHz, d$^6$DMSO) δ(ppm): 7.72–7.65 (m, 2H), 7.50 (d, 1H), 3.17 (s, 3H).

DESCRIPTION 75
2-Methyl-4'-(5-methyl-1,2,4-oxadiazol-3-yl)-1,1'-biphenyl-4-carboxylic acid The title compound was prepared from 3-(4-bromophenyl)-5-methyl-1,2,4-oxadiazole (1 g) and 4-borono-3-methylbenzoic acid (D74, 0.75 g) as a white solid (0.3 g, 24%) by the method described in Description 15.

DESCRIPTION 76
2-(4-Bromophenyl)pyridine

The title compound was prepared from 2-bromopyridine (3 g) and 4-bromophenylboronic acid (3.8 g) by the method described in Description 15 as a pale yellow solid (4.4 g, 98%).

$^1$H NMR (250 MHz, CDCl$_3$) δ(ppm): 8.7 (m, 1H), 7.5–7.95 (m, 6H), 7.2–7.35 (m, 1H).

DESCRIPTION 77
4-(Pyrid-2-yl)phenylboronic acid n-Butyllithium (1.6M in hexane, 2.67 ml) was added to dry ether (16 ml) at −78° C. under argon. A solution of 2-(4-bromophenyl)pyridine (D76, 1.0 g) in dry ether (20 ml) was added dropwise over 5 minutes and allowed to warm to −20° C. for approximately 2 minutes to give a deep red solution. After recooling to −78° C., triisopropylborate (1.18 ml) was added, stirred 30 minutes, warmed to ambient temperature to give a yellow cloudy mixture. Water (4.2 ml) and 0.5 M NaOH (4.2 ml) were added with vigorous stirring and the mixture separated. The ether layer was extracted with 0.5M NaOH (2.8 ml) and the combined aqueous extracts were extracted with ether (2×30 ml). The aqueous layer was acidified to pH6 with dilute hydrochloric acid to give the title compound as a beige solid, (0.15 g, 18%).

$^1$H NMR (250 MHz, d$^6$DMSO) δ(ppm): 8.7 (m, 1H), 7.8–8.2 (m, 6H), 7.4 (m, 1H).

DESCRIPTION 78
3-(4-Bromophenyl)pyridine

The title compound was prepared from 3-bromopyridine (5 g) and 4-bromophenylboronic acid by the method described in Description 15 (2.6 g, 35%).

$^1$H NMR (270 MHz, CDCl$_3$) δ(ppm): 8.8 (d, 1H), 8.6 (d, 1H), 7.8 (dd, 1H), 7.3–7.65 (m, 5H).

DESCRIPTION 79
4-(Pyrid-3-yl)phenylboronic acid

The title compound was prepared from 3-(4-bromophenyl)pyridine (D78, 1.0 g) by a similar method to that described in Description 77 to give the title compound as a white solid (0.13 g, 15%).

DESCRIPTION 80
4-Bromo-3-ethylbenzonitrile

The title compound was prepared from 4-amino-3-ethylbenzonitrile (6 g) as described in Description 63 (8.6 g, 100%).

$^1$H NMR (250 MHz, CDCl$_3$) δ(ppm): 7.65 (d, 1H), 7.52 (d, 1H), 7.3 (dd, 1H), 2.80 (q, 2H), 1.25 (t, 3H).

DESCRIPTION 81
3-(4-Bromo-3-ethylphenyl)-5-methyl-1,2,4-oxadiazole

The title compound was prepared from 4-bromo-3-ethylbenzonitrile (D80, 4 g) as described EP 0533268A1 as a white solid (2.0 g, 41%).

$^1$H NMR (250 MHz, CDCl$_3$) δ(ppm): 7.95 (d, 1H), 7.75 (dd, 1H), 7.62 (d, 1H), 2.85 (q, 2H), 2.7 (s, 3H), 1.3 (t, 3H).

DESCRIPTION 82
4'-(5-Methyl-1,2,4-oxadiazol-3-yl)-2'-ethyl-1,1'-biphenyl-4-carboxylic acid The title compound was prepared as in Description 15 from 3-(4-bromo-3-ethylphenyl)-5-methyl-1,2,4-oxadiazole (D81, 0.8 g) and 4-boronobenzoic acid (0.49 g) as a cream solid (0.66 g, 71%).

$^1$H NMR (250 MHz, d$^6$DMSO) δ(ppm): 7.95–8.1 (m, 3H), 7.9 (dd, 1H), 7.5 (d, 2H), 7.39 (d, 1H), 2.7 (s, 3H), 2.65 (q, 2H), 1.05 (t, 3H).

DESCRIPTION 83
4'-(5-Methyl-1,2,4-oxadiazol-3-yl)-2,2'-dimethyl-1,1'-biphenyl)-4-carboxylic acid The title compound was prepared as described in Description 15 from 3-(-4-bromo-3-methylphenyl)-5-methyl-1,2,4-oxadiazole (0.93 g) and 3-borono-4-methylbenzoic acid (0.66 g) as a solid (0.82 g, 73%) and used without further purification.

DESCRIPTION 84
2'-Methoxy-5'-nitroformanilide

A mixture of formic acid (0.45 ml, 0.012 mole) and acetic anhydride (1.06 ml, 0.011 mole) was stirred at 55° C. under Ar for 2 h, and cooled to room temperature. Dry THF (10 ml) was added. To this solution was added 2-methoxy-5-nitroaniline (0.69 g, 0.004 mole). After stirring for 1 h, the suspension was evaporated in vacuo to leave the title compound as a brown solid (0.80 g, 99%).

$^1$H NMR (200 MHz, CDCl$_3$+d$^6$DMSO) δ(ppm): 9.27 (d, 1H), 8.66 (brs, 1H), 8.51 (s, 1H), 8.02 (dd, 1H), 6.99 (d, 1H), 4.03 (s, 3H).

DESCRIPTION 85
2-Methoxy-N-methyl-5-nitroaniline

2-Methoxy-5-nitroformanilide (D84) (0.80 g, 4.1 mmole) was stirred in dry THF (30 ml) under Ar as borane dimethyl sulphide complex (2M in toluene, 5.3 ml, 10.6 mmole) was added dropwise. The mixture was stirred at reflux for 3 h, cooled and treated with methanol (5 ml). The resultant mixture was stirred for 1 h, acidified (1M HCl in ether, 5 ml), and then stirred at reflux for 1 h. It was then diluted with methanol, evaporated in vacuo, and partitioned between dil. potassium hydroxide solution and ethyl acetate. The organic portion was separated off, dried (Na$_2$SO$_4$) and evaporated in vacuo to give the title compound as a red-orange solid (0.71 g, 95%). $^1$H NMR (250 MHz, CDCl$_3$) δ(ppm): 7.63 (dd, 1H), 7.37 (d, 1H), 6.75 (d, 1H), 4.48 (bs, 1H), 3.95 (s, 3H), 2.94 (d, 3H).

DESCRIPTION 86

2-Chloro-2'-Methoxy-N-methyl-5'-nitroacetanilide

2-Methoxy-N-methyl-5-nitroaniline (D85) (0.68 g, 3.7 mmole) and triethylamine (0.68 ml, 4.9 mmole) were stirred in chloroform (10 ml) as chloroacetyl chloride (0.39 ml, 4.9 mmole) was added. The solution was stirred for 30 min, acidified with 2M HCl, and separated. The organic portion was dried (Na$_2$SO$_4$) and evaporated in vacuo to give the crude title compound as a black solid (1.01 g, quantitative).

$^1$H NMR (250 MHz, CDCl$_3$) δ(ppm): 8.32 (dd, 1H), 8.19 (d, 1H), 7.12 (d, 1H), 4.00 (s, 3H), 3.79 (s, 2H), 3.26 (s, 3H).

DESCRIPTION 87

2-Dimethylamino-2'-methoxy-N-methyl-5'-nitroacetanilide

2-Chloro-2'-methoxy-N-methyl-5'-nitroacetanilide (D86) (1.01 g, 3.9 mmol) and dimethylamine (33% in IMS, 2 ml) were stirred in ethanol (10 ml) for 3 days. After evaporation to dryness in vacuo, the crude product was partitioned between 2M HCl and ethyl acetate. The aqueous portion was basified with potassium carbonate solution, and extracted with chloroform. The extract was dried (Na$_2$SO$_4$) and evaporated in vacuo to give the title compound as a dark oil (0.85 g, 81%).

$^1$H NMR (250 MHz, CDCl$_3$) δ(ppm): 8.28 (dd, 1H), 8.13 (d, 1H), 7.06 (d, 1H), 3.97 (s, 3H), 3.19 (s, 3H), 2.51 (ABq, 2H), 2.18 (s, 6H).

DESCRIPTION 88

N-(2-Methoxy-5-nitrophenyl)-N,N',N'-trimethylethylenediamine

The title compound was prepared from 2-dimethylamino-2'-methoxy-N-methyl-5'-nitroacetanilide (D87) using a procedure similar to that of Description 9. Chromatography on silica gel, eluting with 0–8% methanol/chloroform, gave the title compound as a yellow oil (66%).

$^1$H NMR (200 MHz, CDCl$_3$) δ(ppm): 7.88 (dd, 1H), 7.77 (d, 1H), 6.87 (d, 1H), 3.97 (s, 3H), 3.22 (t, 2H), 2.89 (s, 3H), 2.49 (t, 2H), 2.26 (s, 6H).

DESCRIPTION 89

N-(5-Amino-2-methoxyphenyl)-N,N',N'-trimethylethylenediamine

The title compound was prepared from N-(2-methoxy-5-nitrophenyl)-N,N',N'-trimethylethylenediamine (D88) using a procedure similar to that of Description 2, as a red-brown oil (quantitative).

$^1$H NMR (200 MHz, CDCl$_3$). δ(ppm): 6.66 (d, 1H), 6.35 (d, 1H), 6.27 (dd, 1H), 3.78 (s, 3H), 3.3 (b), 3.17 (t, 2H), 2.78 (s, 3H), 2.48 (t, 2H), 2.25 (s, 6H).

DESCRIPTION 90

N-[2-Methoxy-5-nitrophenyl]-phenylacetamide

A stirred solution of 2-methoxy-5-nitroaniline (4.86 g, 0.029 mole) and triethylamine (5.2 ml, 0.037 mole) in dichloromethane (150 ml) at 0° C. was treated with phenylacetyl chloride (5.0 ml, 0.037 mole). The mixture was stirred for 0.5 h, then treated with water (20 ml), stirred for a further 20 mins., then basified with Na$_2$CO$_3$ and extracted with dichloromethane. The extract was washed with dil. HCl acid/brine, then dried (Na$_2$SO$_4$) and concentrated in vacuo to afford the title compound as a brown solid (9.0 g, 100%).

$^1$H NMR (250 MHz, CDCl$_3$) δ(ppm): 9.29 (d, 1H), 7.98 (dd, 1H), 7.80 (br s, 1H), 7.48–7.31 (m, 5H), 6.86 (d, 1H), 3.85 (s, 3H), 3.80 (s, 2H).

DESCRIPTION 91

3-[4'-Amino-2-methyl-1,1'-biphenyl]-5-methyl-1,2,4-oxadiazole

2'-Methyl-4'-(5-methyl-1,2,4-oxadiazol-3-yl)[1,1'-biphenyl-4-carboxylic acid (E.P. 0533268-A1) (0.800 g, 2.72 mmol) was suspended in dichloromethane (30 ml) and treated with oxalyl chloride (0.356 ml, 4.082 mmol), followed by a drop of dry DMF. The mixture was then stirred at room temperature for 2 h, before being evaporated under reduced pressure and dried in vacuo to give a pale yellow solid. The solid was redissolved in CH$_2$Cl$_2$ (20 ml) cooled to 0° C. and tetrabutylammonium bromide (0.010 g) was then added, followed by a solution of sodium azide (0.220 g, 3.402 mmol) in water (4 ml). The reaction mixture was kept at 0° C. for 2 h and was vigorously stirred. Water (20 ml) was then added, and the organic layer was separated off, dried (Na$_2$SO$_4$) and treated with trifluoroacetic acid (0.326 ml, 4.22 mmol). The reaction mixture was then refluxed overnight. The reaction mixture was then allowed to cool and was washed with NaHCO$_3$ solution. The aqueous layer was extracted with CH$_2$Cl$_2$ and the combined organic layers were then dried (Na$_2$SO$_4$) and evaporated under reduced pressure to give an orange oil that crystallised on standing. The resultant solid was then redissolved in a mixture of 10% NaOH (10 ml) and MeOH (15 ml) and was then heated to reflux with stirring. After 4 h, the reaction mixture was allowed to cool and the methanol present was removed by evaporation under reduced pressure. The aqueous residue was then extracted with CH$_2$Cl$_2$ (2x), and the combined organic layers were dried (Na$_2$SO$_4$) and evaporated under reduced pressure to give a brown oil, which was dried in vacuo. The oil was then purified by silica-gel chromatography (1:1 Petrol:Et$_2$O as eluant) to give the title compound as a colourless oil (0.104 g; 14%) that crystallised on standing.

$^1$H NMR (200 MHz, CDCl$_3$) δ: 7.97 (s, 1H), 7.89 (d, 1H), 7.30 (d, 1H), 7.12 (dd, 2H), 6.70 (dd, 2H), 3.72 (s, 2H), 2.70 (s, 3H), 2.34 (s, 3H).

DESCRIPTION 92

Methyl-3-(2-dimethylamninoethoxy)-4-methoxy benzoate

Methyl 3-hydroxy-4-methoxy benzoate (0.500 g, 2.75 mmol) was dissolved in DME (10 ml) and treated with saturated aqueous potassium carbonate solution (4 ml), followed by 2-dimethylaminoethylchloride hydrochloride salt (0.436 g, 3.03 mmol). The mixture was then treated to reflux with stirring. After 3.5 h, the reaction mixture was allowed to cool and was partitioned between CH$_2$Cl$_2$ and water. The aqueous layer was then extracted with CH$_2$Cl$_2$ and the combined organic layers were dried (Na$_2$SO$_4$) and evaporated under reduced pressure to give the title compound as a colourless oil, which was dried in vacuo (0.640 g, 92%).

$^1$H NMR (250 MHz, CDCl$_3$) δ: 7.70 (dd, 1H), 7.55 (d, 1H), 6.90 (d, 1H), 4.18 (t, 2H), 3.90 (s, 3H), 3.87 (s, 3H), 2.71 (t, 2H), 2.38 (s, 6H).

DESCRIPTION 93

4-(1,2,4-Triazol-1-yl)nitrobenzene

4Fluoronitrobenzene (2 g, 0.014 mol), 1,2,4-triazole (1 g, 0.014 mol), potassium carbonate (1.96 g, 0.014 mol) were dissolved in DMSO (50 ml) and stirred at 90° C. for 24 h under dry conditions. The yellow suspension was poured into water (150 ml), extracted (EtOAc), dried (Na$_2$SO$_4$) and evaporated under reduced pressure to afford an orange solid which was purified by flash column chromatography on silica eluting with n-pentane/ethyl acetate (50–100%) to afford a white solid (2.57 g 97%).

hu 1H NMR (CDCl$_3$) δ 7.95 (2H, d), 8.19 (1H, s), 8.42 (2H, d), 8.71 (1H, s).

DESCRIPTION 94
4-(1,2,4-Triazol-1-yl)aniline 4-(1,2,4-Triazol-1-yl)nitrobenzene (0.5 g, 3 mmol) and Pd/C (500 mg) in ethanol (50 ml) were hydrogenated at rtp for 3 days. The suspension was filtered through celite, evaporated under reduced pressure to afford a white solid (418 mg, 87%).

$^1$H NMR (CDCl$_3$) δ 3.88 (2H, bs, NH$_2$), 6.78 (2H, d), 7.41 (2H, d), 8.05 (1H, s), 8.40 (1H, s).

DESCRIPTION 95
4-(1,2,4-Triazol-1-yl)bromobenzene 4-(1,2,4-Triazol-1-yl)aniline (400 mg, 2.5 mmol) in 48% HBr (10 ml) at −5° C. was stirred while sodium nitrite (173 mg, 2.5 mmol) was added portionwise over 5 minutes. The brown sludge was left stirring for 15 minutes and then added portionwise over 5 minutes to a refluxing mixture of copper (I) bromide (358 mg, 2.5 mmol) in 48% HBr (2 ml). The mixture was then heated at reflux for 1 minute, allowed to cool slightly, and poured into 10% ethylene diamine solution (20 ml). The aqueous solution was extracted with ethyl acetate, dried (Na$_2$SO$_4$), and evaporated to dryness under reduced pressure. The resulting mixture was purified by column chromatography on silica eluting with n-pentane/ethyl acetate (4–10%) to afford the title compound as a white solid (344 mg, 61%).

$^1$H NMR (CDCl$_3$) δ 7.62 (4H, q), 8.13 (1H, s), 8.58 (1H, s).

DESCRIPTION 96
4'-(1,2,4-Triazol-1-yl)-(1,1'-biphenyl)-4-carboxylic acid 4-(1,2,4-Triazol-1-yl)bromobenzene (340 mg, 1.5 mmol), 4-carboxylic acid benzene boronic acid (250 mg, 1.5 mmol), sodium carbonate (650 mg, 4 eq), tetrakis(triphenylphosphine)palladium(0) (50 mg) in DME (25 ml) and water (25 ml) was heated under argon at reflux for 24 h, cooled, evaporated to dryness under reduced pressure, partitioned between saturated aqueous sodium carbonate solution (50 ml) and ethyl acetate (50 ml), the aqueous extracts acidified with conc. HCl and dried in vacuo to afford the title compound as a pale yellow crystalline solid (367 mg, 92%).

$^1$H NMR (d$_6$DMSO) δ 7.48 (4H, q), 7.98 (4H, q), 8.20 (1H, s), 9.32 (1H, s).

DESCRIPTION 97
4-(Tetrazol-2-yl)nitrobenzene

4-Fluoronitrobenzene (2 g, 0.014 mol), tetrazole (1 g, 0.014 mol), potassium carbonate (1.96 g, 0.014 mol) were dissolved in DMSO (50 ml) and stirred at 90° C. for 24 h under dry conditions. The yellow suspension was poured into water (150 ml), the resulting yellow solid filtered of and dried in vacuo to afford the title compound (831 mg, 31%).

$^1$H NMR (CDCl$_3$) δ 8.01 (2H, d), 8.52 (2H, d), 9.15 (1H, s).

DESCRIPTION 98
4-(Tetrazol-2-yl)aniline 4-(Tetrazol-2-yl)nitrobenzene (0.83 g, 4.3 mmol) and Pd/C (300 mg) in ethanol (50 ml) were hydrogenated at rtp for 3 days. The suspension was filtered through celite, evaporated under reduced pressure to afford a white solid (790 mg, 100%).

$^1$H NMR (CDCl$_3$) δ 4.00 (2H, bs, NH$_2$), 6.80 (2H, d), 7.90 (2H, d), 8.60 (1H, s).

DESCRIPTION 99
4-(Tetrazol-2-yl)bromobenzene 4-(Tetrazol-2-yl)aniline (450 mg, 2.8 mmol) in 48% HBr (10 ml) at −5° C. was stirred while sodium nitrite (193 mg, 2.8 mmol) was added portionwise over 5 minutes. The brown sludge was left stirring for 15 minutes and then added portionwise over 5 minutes to a refluxing mixture of copper (I) bromide (401 mg, 2.8 mmol) in 48% HBr (2 ml). The mixture was then heated at reflux for 1 minute, allowed to cool slightly, and poured into 10% ethylene diamine solution (20 ml). The aqueous solution was extracted with ethyl acetate, dried (Na$_2$SO$_4$), and evaporated to dryness under reduced pressure. The resulting mixture was purified by column chromatography on silica eluting with n-pentane/ethyl acetate (4–10%) to afford the title compound as a white solid (238 mg, 38%).

$^1$H NMR (CDCl$_3$) δ 7.71 (2H, d), 8.06 (2H, d), 8.68 (1H, s).

DESCRIPTION 100
4'-(Tetrazol-2-yl)-(1,1'-biphenyl)-4-carboxylic acid

4'-(Tetrazol-2-yl)bromobenzene (200 mg, 0.89 mmol), 4-carboxylic acid benzene boronic acid (148 mg, 0.89 mmol), sodium carbonate (377 mg, 4 eq), tetrakis(triphenylphosphine)palladium(0) (50 mg) in DME (18 ml) and water (1 8 ml) was heated under argon at reflux for 24 h, cooled, evaporated to dryness under reduced pressure, partitioned between saturated aqueous sodium carbonate solution (50 ml) and ethyl acetate (50 ml), the aqueous extract acidified with conc. HCl, the resulting solid filtered and dried under vacuum to afford a beige solid (171 mg, 72%).

$^1$H NMR (d$_6$DMSO) δ 7.90 (2H, d), 8.07 (4H, m), 8.25 (2H, d), 9.32 (1H, s).

DESCRIPTION 101
2-Methyl-4-(1,2,4-triazol-1-yl)nitrobenzene

4-Fluoro-2-methyl-nitrobenzene (2 g, 0.013 mol), 1,2,4-triazole (0.9 g, 0.013 mol), potassium carbonate (1.78 g, 0.013 mol) were dissolved in DMSO (50 ml) and stirred at 90° C. for 24 h under dry conditions. The yellow suspension was poured into water (150 ml), extracted (EtOAc), dried (Na$_2$SO$_4$) and evaporated under reduced pressure to afford an orange solid which was purified by flash column chromatography on silica eluting with n-pentane/ethyl acetate (50–100%) to afford a white solid (2.83 g 69%).

$^1$H NMR (CDCl$_3$) δ 2.72 (3H, s), 7.70 (1H, dd), 7.78 (1H, s), 8.18 (1H, 2), 8.20 (1H, s), 8.68 (1H, s).

DESCRIPTION 102
2-Methyl-4-(1,2,4-triazol-1-yl)aniline

2-Methyl-4-(1,2,4-Triazol-1-yl)nitrobenzene (1.0 g, 4.9 mmol) and Pd/C (200 mg) in ethanol (50 ml) were hydrogenated at rtp for 3 days. The suspension was filtered through celite, evaporated under reduced pressure to afford a white solid (850 mg, 100%).

DESCRIPTION 103
2-Methyl-4-(1,2,4-triazol-1-yl)bromobenzene

2-Methyl-4-(1,2,4-triazol-1-yl)aniline (550 mg, 4.4 mmol) in 48% HBr (10 ml) at 5° C. was stirred while sodium nitrite (304 mg, 4.4 mmol) was added portionwise over 5 minutes. The brown sludge was left stirring for 15 minutes and then added portionwise over 5 minutes to a refluxing mixture of copper (I) bromide (631 mg, 4.4 mmol) in 48% HBr (2 ml). The mixture was then heated at reflux for 1 minute, allowed to cool slightly, and poured into 10% ethylene diamine solution (20 ml). The aqueous solution was extracted with ethyl acetate, dried (Na$_2$SO$_4$), and evaporated to dryness under reduced pressure. The resulting mixture was purified by column chromatography on silica eluting with n-pentane/ethyl acetate (4–10%) to afford the title compound as a white solid (0.769 mg, 73%).

¹H NMR (CDCl₃) δ 2.49 (3H, s), 7.39 (1H, dd), 7.60 (1H, dd), 7.65 (1H, d) 8.10 (1H, s), 8.51 (1H, s).

EXAMPLE 1
N-[3-(Dimethylaminoethoxy)-4-methoxyphenyl]-2'-methyl-4'-(5-methyl-1,2,4-oxadiazol-3-yl)biphenyl-4-carboxamide A stirred solution of 2'-methyl-4'-(5-methyl-1,2,4-oxadiazol-3-yl)-biphenyl-4-carboxamide (EP 0533268A') (0.13 g, 0.00048 mol) in thionyl chloride (5 ml) was heated under reflux for 1 hour. After cooling to room temperature, the solvent was removed in vacuo.

2-(Dimethylaminoethoxy)-4-methoxyaniline (D2) (0.10 g, 0.00048 mol) in THF (5 ml) was treated with a solution of sodium hydroxide (0.04 g) in H₂O (0.6 ml) and the acid chloride in THF (5 ml) was added. The mixture was stirred overnight at room temperature.

After removal of the solvent in vacuo, the residue was dissolved in CH₂Cl₂, washed (×3) with H₂O dried (MgSO₄) and evaporated in vacuo. Flash column chromatography on silica gel eluting with CH₂Cl₂/MeOH gave the title compound as a white solid (0.10 g, 43%) mp=143°–144° C.

¹H NMR (250 MHz; CDCl₃) δ(ppm): 8.07 (m, 5H), 7.55–7.40 (m, 3H), 7.35 (d, 1H), 7.08 (dd, 1H), 6.87 (d, 1H), 4.18 (t, 2H), 3.87 (s, 3H), 2.82 (t, 2H), 2.70 (s,3H), 2.38 (s, 9H).

EXAMPLE 2
N-[3-(2-Diethiylaminoethoxy)-4-methoxyphenyl]-2'-methyl-4'-(5-methyl-1,2,4-oxadiazol-3-yl)biphenyl-4-carboxamide The title compound was prepared from 2'-methyl-4'-(5-methyl-1,2,4-oxadiazol-3-yl)biphenyl-4-carboxylic acid (EP 0533268 A1) and 3-(2-diethylaminoethoxy)-4-methoxyaniline (D3) using a similar procedure to Example 1 (68%). This was converted to its oxalate salt mp 158°–162° C.

¹H NMR oxalate salt (250 MHz, d⁶DMSO) δ(ppm): 10.30 (s, 1H), 8.06 (d, 2H), 7.95 (s, 1H), 7.90 (d, 1H), 7.65–7.50 (m, 3H), 7.47–7.33 (m, 2H), 7.00 (d, 1H), 4.30 (brt, 2H), 3.78 (s, 3H), 3.7–3.3 (2H), 3.25 (q, 4H), 2.68 (s, 3H), 2.35 (s, 3H), 1.25 (t, 6H)

EXAMPLE 3
N-[3-(2-Diisopropylaminoethoxy)-4-methoxyphenyl]-2'-methyl-4'-(5-methyl-1,2,4-oxadiazol-3-yl)biphenyl-4-carboxamide The title compound was prepared from 2'-methyl-4'-(5-methyl-1,2,4-oxadiazol-3-yl)biphenyl-4-carboxylic acid (EP 0533268 A1) and 3-(2-diisopropylaminoethoxy)-4-methoxyaniline (D4) following a procedure similar to that described in Example 1 (27%) mp 130°–131° C.

¹H NMR (250 MHz, CDCl₃) δ(ppm): 8.00 (s, 1H), 7.97–7.92 (m, 3H), 7.80 (s, 1H), 7.48 (d, 2H), 7.40–7.32 (m, 2H), 7.11 (d, 1H), 6.88 (d, 1H), 3.98 (t, 2H), 3.89 (s, 3H), 3.12–3.01 (m, 2H), 2.94 (t, 2H), 2.70 (s,3H), 2.33 (s, 3H), 1.06 (d, 12H)

EXAMPLE 4
N-[3-(2-Dimethylamino-1-methylethoxy)-4-methoxyphenyl]-2'-methyl-4'-(5-methyl-1,2,4-oxadiazol-3-yl)biphenyl-4-carboxamide The title compound was prepared from 2'-methyl-4'-(5-methyl-1,2,4-oxadiazol-3-yl)biphenyl-4-carboxylic acid (EP 0533268 A1) and 3-(2-dimethylamino-1-methylethoxy)-4-methoxyaniline (D6) using a similar procedure to Example 1 (61 %) mp 60°–65° C.

¹H NMR (250 MHz, CDCl₃) δ(ppm): 8.05–7.90 (m, 4H), 7.80 (s, 1H), 7.55–7.45 (m, 3H), 7.36 (d, 1H), 7.13 (dd, 1H), 6.89 (d, 1H), 4.60 (sextet, 1H), 3.86 (s, 3H), 2.77 (dd, 1H), 2.69 (s, 3H), 2.52 (dd, 1H), 2.37 (s, 6H), 2.35 (s, 3H), 1.37 (d, 3H).

EXAMPLE 5
N-[3-(2-Dimethylaminopropoxy)-4-methoxyphenyl]-2'-methyl-4'-(5-methyl-1,2,4-oxadiazol-3-yl)biphenyl-4-carboxamide The title compound was prepared from 2'-methyl-4'-(5-methyl-1,2,4-oxadiazol-3-yl)biphenyl-4-carboxylic acid (EP 0533268 A1) and 3-(2-dimethylaminopropoxy)-4-methoxyaniline (D7) using a similar procedure to Example 1 (34%) mp 105°–110° C.

¹H NMR (250 MHz, CDCl₃) δ(ppm): 8.43 (s, 1H), 8.02–7.85 (m, 4H), 7.49 (brd, 1H), 7.39 (d, 2H), 7.27 (d, 1H), 7.13 (dd, 1H), 6.80 (d, 1H), 4.13–4.02 (m, 1H), 3.92–3.82 (m, 1H), 3.77 (s, 3H), 3.10 (sextet, 1H), 2.63 (s, 3H), 2.35 (s, 6H), 2.27 (s, 3H), 1.12 (d, 3H)

EXAMPLE 6
N-[3-(2-Methylaminoethoxy)-4-methoxyphenyl]-2'-methyl-4'-(5-methyl-1,2,4-oxadiazol-3-yl)biphenyl-4-carboxamide A solution of N-[3-(2-dimethylaminoethoxy)-4-methoxyphenyl]-2'-methyl-4'-(5-methyl-1,2,4-oxadiazol-3-yl)biphenyl-4-carboxamide (E1, 0.2 g, 0.41 mmole) in 1,2-dichloroethane (5 ml) was treated at room temperature with 1-chloroethyl chloroformate (0.12 ml, 1.12 mmole) followed by diisopropylethylamine (0.15 ml, 0.86 mmole). The mixture was stirred for 2 hours at room temperature. After removal of solvent in vacuo the residue was treated with methanol (8 ml) and heated under reflux for 30 minutes. The reaction mixture was concentrated in vacuo and the residue treated with saturated aqueous potassium carbonate (10 ml) and extracted with dichloromethane (3×10 ml). The combined organic extracts were dried and concentrated in vacuo. Flash column chromatography on silica gel eluting with 5% MeOH/CH₂Cl₂ gave the title compound as a light pink solid (0.13 g, 68%) mp 97°–99° C.

¹H NMR (250 MHz, CDCl₃) δ(ppm): 8.15 (s, 1H), 8.01–7.92 (m, 4H), 7.53–7.41 (m, 3H), 7.33 (d, 1H), 7.20 (dd, 1H), 6.82 (d, 1H), 4.20 (t, 2H), 3.85 (s, 3H), 3.10 (t, 2H), 2.69 (s, 3H), 2.60 (s, 3H), 2.32 (s, 3H).

EXAMPLE 7
N-[3-(2-Aminoethoxy)-4-methoxyphenyl]-2'-methyl-4'-(5-methyl-1,2,4-oxadiazol-3-yl)biphenyl-4-carboxamide 2'-methyl-4'-(5-methyl-1,2,4-oxadiazol-3-yl)biphenyl-4-carboxylic acid (EP 0533268 A1) was reacted with 3-(2-(t-butyloxycarbonylamino)ethoxy)-4-methoxyaniline (D11) following a procedure similar to that described in Example 1. The product was dissolved in methanol (10 ml), and treated with 3.3M ethereal HCl solution (3 ml) and left to stand at room temperature for 20 hours. After removal of the solvent in vacuo, the residue was dissolved in H₂O solid potassium carbonate was added and the mixture extracted with EtOAC (3×). The combined organic extracts were dried and concentrated in vacuo. Flash column chromatography on silica gel eluting with 5% MeOH/CH₂Cl₂ gave the title compound as a white solid (0.06 g, 19%) mp 150°–153° C.

¹H NMR (250 MHz, CDCl₃) δ(ppm): 8.00 (s, 1H), 7.95–7.92 (m, 3H), 7.82 (s, 1H), 7.52–7.45 (m 3H), 7.34 (d, 1H), 7.06 (dd, 1H), 6.89 (d, 1H), 4.10 (t, 2H), 3.89 (s, 3H), 3.12 (t, 2H), 2.70 (s, 3H), 2.35 (s, 3H), 1.55 (brs, 2H)

EXAMPLE 8
N-[3-(2-Piperidin-1-ylethoxy)-4-methoxyphenyl]-2'-methyl-4'-(5-methyl-1,2,4-oxadiazol-3-yl)biphenyl-4-carboxamide The title compound was prepared from 2'-methyl-4'-(5-methyl-1,2,4,oxadiazol-3-yl)biphenyl-4-carboxylic acid (EP 0533268 A1) and 3-(2-piperidin-1-ylethoxy)-4-methoxyaniline (D12) using a similar procedure to Example 1, as a light brown solid (30%) mp 96°–99° C.

$^1$H NMR (250 MHz, CDCl$_3$) δ(ppm): 8.05–7.90 (m, 4H), 7.81 (s, 1H), 7.52–7.42 (m, 3H), 7.36 (d, 1H), 7.08 (dd, 1H), 6.87 (d, 1H), 4.20 (t, 2H), 3.87 (s, 3H), 2.85 (t, 2H), 2.69 (s, 3H), 2.60–2.45 (m, 4H), 2.35 (s, 3H), 1.68–1.53 (m, 4H), 1.50–1.38 (m, 2H)

EXAMPLE 9
N-[3-(2-Morpholin-4-ylethoxy)-4-methoxyphenyl]-2'-methyl-4'-(5-methyl-1,2,4-oxadiazol-3-yl)biphenyl-4-carboxamide The title compound was prepared from 2'-methyl-4'-(5-methyl-1,2,4-oxdiazol-3-yl)biphenyl-4-carboxylic acid (EP 0533268 A1) and 3-(2-morpholin-4-ylethoxy)-4-methoxyaniline (D13) using a similar procedure to Example 1 (58%) mp 58°–63° C.

$^1$H NMR (250 MHz, CDCl$_3$) δ(ppm): 8.60 (s, 1H), 8.05–7.87 (m, 4H), 7.59 (d, 1H), 7.35 (d, 2H), 7.28 (d, 1H), 7.12 (dd, 1H), 6.82 (d, 1H), 4.12 (t, 2H), 3.80 (s, 3H), 3.78–3.63 (m, 4H), 2.80 (t, 2H), 2.65 (s, 3H), 2.60–2.50 (m, 4H), 2.29 (s, 3H)

EXAMPLE 10
N-[3-(2-Dimethylaminoethoxy)-4-methoxyphenyl]-2'-methyl-4'-(3-methyl-1,2,4-oxadiazol-5-yl)biphenyl-4-carboxamide The title compound was prepared from 2'-methyl-4'-(3-methyl-1,2,4-oxadiazol-5-yl)biphenyl-4-carboxylic acid (D15) and 2-(2-dimethylaminoethoxy)-4-methoxyaniline (D2) using a similar procedure to Example 1, as a white solid (21%) mp 160°–162° C.

$^1$H NMR (250 MHz, CDCl$_3$: δ(ppm): 8.30 (s, 1H), 8.10–7.94 (m, 4H), 7.50 (d, 1H), 7.46–7.28 (m, 3H), 7.12 (dd, 1H), 6.85 (d, 1H), 4.12 (t, 2H), 3.38 (s, 3H), 2.77 (t, 2H), 2.50 (s, 3H), 2.34 (s, 3H), 2.30 (s, 6H)

EXAMPLE 11
N-[3-(2-Dimethylaminoethoxy)-4-methoxyphenyl]-2'-methyl-4'-(5-methyl-1,3,4-oxadiazol-2-yl)biphenyl-4-carboxamide The title compound was prepared from 2'-methyl-4'-(5-methyl-1,3,4-oxadiazol-2-yl)biphenyl-4-carboxylic acid (D16), following a procedure similar to that described in Example 1 (75%) mp 152°–159° C.

$^1$H NMR (250 MHz, CDCl$_3$) δ(ppm): 8.00–7.90 (m, 4H), 7.82 (s, 1H), 7.52–7.48 (m, 3H), 7.39 (d, 1H), 7.10 (dd, 1H), 6.98 (d, 1H), 4.20 (t, 2H), 3.87 (s, 3H), 2.85 (t, 2H), 2.63 (s, 3H), 2.40 (s, 6H), 2.37 (s, 3H)

EXAMPLE 12
N-[3-(2-Dimethylaminoethoxy)-4-methoxyphenyl]-2'-methyl-4'-(1,3,4-oxadiazol-2-yl)biphenyl-4-carboxamide A solution of N-[3-(2-dimethylaminoethoxy)-4-methoxyphenyl]-4'-methoxycarbonyl-2'-methylbiphenyl-carboxamide (D23, 0.14 g, 0.3 mmole) in methanol (5 ml) was treated with hydrazine hydrate (0.21 ml) and heated under reflux for 2 days. The mixture was allowed to cool, then poured into water (50 ml) and the precipitated solid filtered off and dried. This was treated with triethylorthoformate (5 ml) and heated under reflux for 18 hours, then concentrated in vacuo. The residue was purified by preparative TLC on a silica gel plate eluting with 10% methanol/dichloromethane to afford the title compound (40 mg,28%). This was converted to its oxalate salt mp 185°–193° C.

$^1$H NMR free base (250 MHz, CDCl$_3$) δ(ppm): 8.45 (s, 1H), 8.20 (brs, 1H), 8.00–7.85 (m, 4H), 7.45–7.28 (m, 4H), 7.15 (dd, 1H), 6.79 (d, 1H), 4.12 (t, 2H), 3.78 (s, 3H), 2.82 (t, 2H), 2.35 (s, 6H), 2.28 (s, 3H)

EXAMPLE 13
N-[3-(2-Dimethylaminoethoxy)phenyl]-2'-methyl-4'-(5-methyl-1,2,4-oxadiazol-3-yl)biphenyl-4-carboxamide The title compound was prepared from 2'-methyl-4'-(5-methyl-1,2,4-oxadiazol-3-yl)biphenyl-4-carboxylic acid [EP 0533268 A1] following a procedure similar to that described in Example 1 (61%) mp 98°–100° C.

$^1$H NMR (250 MHz; CDCl$_3$) δ(ppm): 8.1–7.9 (m, 4H), 7.85 (s, 1H), 7.57–7.42 (m, 3H), 7.35 (d, 1H), 7.3–7.22 (m, 1H), 7.11 (d, 1H), 6.75 (d, 1H), 4.12 (t, 2H), 2.7 (s, 3H), 2.36 (s, 9H)

EXAMPLE 14
N-[5-(2-Dimethylaminoethoxy)-2,4-diiodophenyl]-2'-methyl-4'-(5-methyl-1,2,4-oxadiazol-3-yl)biphenyl-4-carboxamide A solution of N-[3-(2-dimethylaminoethoxy)phenyl]-2'-methyl-4'-(5-methyl-1,2,4-oxadiazol-3-yl)biphenyl-4-carboxamide (E13) (100 mg) in glacial acetic acid (2 ml) was treated with iodine monochloride (46 mg) and refluxed for 2 h. The mixture was cooled to room temperature and treated sequentially with sodium sulphite, the saturated aqueous sodium bicarbonate and extracted into ethyl acetate. The organic extract was dried over Na$_2$SO$_4$ and the solvent evaporated under reduced pressure. The residue was purified by flash silica chromatography, eluting with methanol and dichloromethane, to give the title compound as a cream powder (74 mg, 58%) mp 69°–71° C.

$^1$H NMR (200 MHz; CDCl$_3$) δ(ppm): 8.4 (s, 1H), 8.3 (s, 1H), 8.14 (s, 1H), 8.06–7.91 (m, 4H), 7.58–7.48 (m, 2H), 7.36 (d, 1H), 4.46 (brs, 1H), 4.25 (t, 2H), 2.92 (t, 2H), (s, 2.69 3H), 2.45 (s, 6H), 2.35 (s, 3H)

EXAMPLE 15
N-[3-[(2-Dimethylaminoethyl)amino]-4-methoxyphenyl]-2'-methyl-4'-(5-methyl-1,2,4-oxadiazol-3-yl)-biphenyl-4-carboxamide oxalate N-[3-[N-(2-Dimethylamineothyl)-N-t-butyloxycarbonylamino]-4-methoxyphenyl]-2'-methyl-4'-(5-methyl-1,2,4-oxadiazol-3-yl)biphenyl-4-carboxamide (D22, 0.40 g, 0.00068 mole) was dissolved in dichloromethane (20 ml) and TFA (5 ml). The solution was stirred at ambient temperature for 2 h hours, and the solvent was removed in vacuo. The residue was dissolved in CH$_2$Cl$_2$, washed with saturated aqueous sodium hydrogen carbonate solution, dried (Na$_2$SO$_4$) and evaporated in vacuo. The residue was purified by flash column chromatography on silica gel, eluting with MeOH/CH$_2$Cl$_2$, and treated with oxalic acid to leave the title compound as an off white solid (0.25 g, 76%)

$^1$H NMR (250 MHz; CDCl$_3$) δ(ppm): 10.08 (s, 1H), 8.05 (d, 2H), 8.00 (s, 1H), 7.92 (d, 1H), 7.57 (d, 2H), 7.44 (d, 1H), 7.11 (m, 2H), 6.82 (d, 2H), 5.51–3.90 (brs, 2H), 3.78 (s, 3H), 3.41 (t, 2H), 3.27 (t, 2H), 2.79 (s, 6H), 2.70 (s, 3H), 2.36 (s, 3H)

EXAMPLE 16
N-[3-(3-Dimethylaminopropoxy)-4-methoxyphenyl]-2'-methyl-4'-(5-methyl-1,2,4-oxadiazol-3-yl)biphenyl-4-carboxamide The title compound was prepared from 2'-methyl-4'-(5-methyl-1,2,4-oxadiazol-3-yl)biphenyl-4-carboxylic acid (EP 0533268 A1) and 3-(3-dimethylaminopropoxy)-4-methoxyaniline (D23) using a similar procedure to Example 1 (58%).

¹H NMR (250 MHz; CDCl₃) δ(ppm): 8.12–7.88 (m, 5H), 7.59–7.41 (m, 3H), 7.35 (d, 1H), 7.15 (dd, 1H), 6.88 (d, 1H), 4.12 (t, 2H), 3.88 (s, 3H), 2.70 (s, 3H), 2.55 (t, 2H), 2.35 (s, 3H), 2.55 (t, 2H), 2.35 (s, 3H), 2.32 (s, 6H),2.19–1.99 (m, 2H)

EXAMPLE 17

N-[3-(3-Dimethylaminopropyl)-4-methoxyphenyl]-2'-methyl-4'-(5-methyl-1,2,4-oxadiazol-3-yl)biphenyl-4-carboxamide 2'-Methyl-4'-(5-methyl-1,2,4-oxadiazol-3-yl)biphenyl-4-carboxylic acid (E. P. 0533268A 1) (0.212 g, 0.721 mmol) was suspended in dichloromethane (5 ml) and treated with oxalyl chloride (0.094 ml, 1.08 mmol), followed by a drop of dry DMF with stirring. After 4 h, the reaction mixture was evaporated under reduced pressure and dried in vacuo to give the crude acid chloride as a yellow solid. Meanwhile to a solution of the product from description 2 (0.142 g, 0.683 mmol) in dichloromethane (10 ml); triethylamine (0.095 ml, 0.683 mmol) was added, followed by a solution of the crude acid chloride in dichloromethane (4 ml), with stirring. After 1 h, the reaction mixture was washed with water (1×), followed by sodium bicarbonate solution (1×). The organic layer was then dried (Na₂SO₄) and evaporated under reduced pressure to give a brown oil which was dried in vacuo. The oil was purified by SiO₂ chromatography (7.5% MeOH in CH₂Cl₂ as eluant) to give the title compound as a pale yellow oil (0.052 g, 16%) which was converted to its oxalate salt. m.pt 144°–148° C. (oxalate salt)

¹H NMR (270 MHz, CD₃SOCD₃) δ(ppm): (oxalate salt) 10.20 (s, 1H), 8.08 (d, 2H), 7.98 (s, 1H), 7.91 (d, 1H), 7.65 (d, 2H), 7.58 (d, 2H), 7.45 (d, 1H), 7.00 (d, 1H), 3.80 (s, 3H), 3.08 (t, 2H), 2.75 (s, 6H), 2.65 (s, 3H), 2.58 (t, 2H), 2.32 (s, 3H), 1.90 (m, 2H)

EXAMPLE 18

N-[3-(3-Dimethylaminoprop-1-enyl)-4-methoxyphenyl]-2'-methyl-4'-(5-methyl -1,2,4-oxadiazol-3-yl)biphenyl-4-carboxamide The product from description 3 (0.090 g, 0.437 mmol) was transformed to give the title compound (0.07 g, 33%) as a white foam, which was converted to its oxalate salt according to the method described in Example 1. m.pt. 220°–221° C. (oxalate salt)

¹H NMR (250 MHz, CDCl₃) δ(ppm): (free base) 7.98 (m, 5H), 7.68 (dd, 1H), 7.60 (d, 1H), 7.48 (d, 2H), 7.35 (d, 1H), 6.90 (s, 1H), 6.85 (d, 1H), 6.35 (m, 1H), 3.83 (s, 3H), 3.32 (d, 2H), 2.70 (s, 3H), 2.38 (s, 6H), 2.32 (s, 3H).

EXAMPLE 19

N-[4-(3-Dimethylaminopropoxy)phenyl]-2'-methyl-4'-(5-methyl-1,2,4-oxadiazol-3-yl)biphenyl-4-carboxamide The title compound was prepared from 2'-methyl-4'-(5-methyl-1,2,4-oxadiazol-3-yl)biphenyl-4-carboxylic acid (EP 0533268 A1) and 4-(3-dimethylaminopropoxy) aniline (D29) using a similar procedure to Example 20 (38%), as an off-white solid mp 162°–165° C.

¹H NMR (250 MHz, CDCl₃) δ(ppm): 8.20 (s, 1H), 8.00–7.90 (m, 3H), 7.80 (s, 1H), 7.56 (d, 2H), 7.48 (d, 2H), 7.37 (d, 1H), 6.94 (d, 2H), 4.03 (t, 2H), 2.70 (s, 3H), 2.50 (t, 2H), 2.35 (s, 3H), 2.30 (s, 6H), 2.00 (quintet, 2H).

EXAMPLE 20

N-[3-(2-Pyrrolidin-1-ylethoxy)-4-methoxyphenyl]-2'-methyl-4'-(5-methyl-1,2,4-oxadiazol-3-yl)biphenyl-4-carboxamide A stirred suspension of 2'-methyl-4'-(5-methyl-1,2,4-oxadiazol-3-yl)biphenyl-4-carboxylic acid (EP 0533268A1) (300 mg, 1.0 mmole) in dichloromethane (20 ml) at room temperature under argon was treated with oxalyl chloride (0.13 ml, 1.5 mmoles), followed by DMF (1 drop). The mixture was stirred for 2 h, then concentrated in vacuo to leave the acid chloride as a pale yellow solid. This was dissolved in dichloromethane (8 ml) and added to a stirred solution of 3-(2-pyrrolidin-1-ylethoxy)-4-methoxyaniline (D31, 240 mg, 1.0 mmole) and triethylamine (0.28 ml, 2.0 mmoles) in dichloromethane (20 ml) at 5° C. under argon. The reaction mixture was allowed to warm to room temperature and stir for 2 h, then treated with 10% Na₂CO₃ solution (20 ml) and extracted with dichloromethane (2×30 ml). The combined extract was dried (Na₂SO₄), concentrated in vacuo and the residue chromatographed on silica gel eluting with 3% methanol/chloroform. The title compound crystallised from ethyl acetate/60–80 petrol ether (1.30 g, 25%) as a white solid mp 111°–112° C.

¹H NMR (250 MHz, CDCl₃) δ(ppm): 8.27 (br s, 1H), 8.03–7.90 (m, 4H), 7.48 (d, 1H), 7.41 (d, 2H), 7.32 (d, 1H), 7.12 (dd, 1H), 6.83 (d, 1H), 4.16 (t, 2H), 3.82 (s, 3H), 2.94 (t, 2H), 2.67 (s, 3H), 2.65–2.52 (m, 4H), 2.32 (s, 3H), 1.83–1.70 (m, 4H).

EXAMPLE 21

N-[3-(2-Dimethylaminoethoxy)-4-methoxyphenyl]-2'-methyl-4'-(5-ethyl-1,2,4-oxadiazol-3-yl)biphenyl-4-carboxamide The title compound was prepared from 2'-methyl-4'-(5-ethyl-1,2,4-oxadiazol-3-yl)biphenyl-3-yl)biphenyl-4-carboxylic acid (D34) and 3-(2-dimethylaminoethoxy)-4-methoxyaniline (D2) using a similar procedure to Example 20 (29%), as a white solid mp 109°–111° C.

¹H NMR (250 MHz, CDCl₃) δ(ppm): 8.05–7.85 (m, 5H), 7.52–7.42 (m, 3H), 7.34 (d, 1H), 7.08 (dd, 1H), 6.87 (d, 1H), 4.17 (t, 2H), 3.87 (s, 3H), 3.02 (q, 2H), 2.80H), 2.35 (s, 9H), 1.48 (t, 3H).

EXAMPLE 22

N-[3-(2-Dimethylaminoethoxy)-4-methoxyphenyl]-2'-methyl-4'-(5-dimethylamino-1,2,4-oxadiazol-3-yl) biphenyl-4-carboxamide The title compound was prepared from 2'-methyl-4'-(5-dimethylamino-1,2,4-oxadiazol-3-yl)biphenyl-4-carboxylic acid (D36) and 3-(2-dimethylaminoethoxy)-4-methoxyaniline (D2) using a similar procedure to Example 20 (21 %) as a white solid mp 106°–108° C.

¹H NMR (250 MHz, CDCl₃) δ(ppm): 8.20 (s, 1H), 7.97–7.84 (m, 4H), 7.50 (d, 1H), 7.40 (d, 2H), 7.27 (d, 1H), 7.12 (dd, 1H), 6.84 (d, 1H), 4.12 (t, 2H), 3.83 (s, 3H), 3.21 (s, 6H), 2.87 (t, 2H), 2.31 (s, 6H), 2.30 (s, 3H).

EXAMPLE 23

N-[3-(2-Dimethylaminoethoxy)-4-methoxyphenyl]-2'-methyl-4'-(4-methylthiazol-2-yl)biphenyl-4-carboxamide The title compound was prepared from 2'-methyl-4'-(4-methylthiazol-2-yl)biphenyl-4-carboxylic acid (D40) and 3-(2-dimethylaminoethoxy)-4-methoxyaniline (D2) using a similar procedure to Example 20 (33%), as an off-white solid mp 155°–156° C.

¹H NMR (250 MHz, d⁶DMSO) δ(ppm): 10.18 (s, 1H), 8.05 (d, 2H), 7.93–7.79 (m, 2H), 7.61–7.49 (m, 3H), 7.42–7.30 (m, 3H), 6.95 (d, 1H), 4.03 (t, 2H), 3.75 (s, 3H), 2.69 (t, 2H), 2.45 (s, 3H), 2.35 (s, 3H), 2.25 (s, 6H).

EXAMPLE 24

N-[3-(2-Dimethylaminoethoxy)-4-methoxyphenyl]-2'-methyl-4'-pyrazinyl biphenyl-4-carboxamide The title compound was prepared from 2'-methyl-4'-pymzinylbiphenyl-4-carboxylic acid (D44) and 3-(dimethylaminoethoxy)-4-methoxyaniline (D2) using a similar procedure to Example 20 (15%) as a white solid mp 173°–175° C.

$^1$H NMR (200 MHz, CDCl$_3$) δ(ppm): 9.07 (s, 1H), 8.65 (d, 1H), 8.53 (d, 1H), 8.23 (s, 1H), 8.03–7.83 (m, 4H), 7.52–7.40 (m, 3H), 7.36 (d, 1H), 7.15 (dd, 1H), 6.84 (d, 1H), 4.12 (t, 2H), 3.83 (s, 3H), 2.82 (t, 2H), 2.35 (s, 3H), 2.33 (s, 6H).

EXAMPLE 25
N-[3-(2-Dimethylaminoethylthio)-4-methoxyphenyl]-2'-methyl-4'-(5-methyl-1,2,4-oxadiazol-3-yl)biphenyl-4-carboxamide (E25)

The title compound was prepared from 2'-methyl-4'-(5-methyl-1,2,4-oxadiazol-3-yl)biphenyl-4-carboxylic acid (EP 0533268 A1) and 4-amino-2-(2-dimethylaminoethylthio)anisole (D48) using a similar procedure to Example 1 (50%) mp 138°–9° C.

$^1$H NMR (250 MHz, CDCl$_3$) δ(ppm): 8.03–7.91 (m, 5H), 7.6–7.42 (m, 4H), 7.34 (d, 1H), 6.85 (d, 1H), 3.89 (s, 3H), 3.1–3.0 (m, 2H), 2.69 (s, 3H), 2.67–2.58 (m, 2H), 2.34 (s, 3H), 2.29 (s, 6H)

EXAMPLE 26
N-[3-(2-Dimethylaminoethylsulphinyl)-4-methoxyphenyl]-2'-methyl-4'-(5-methyl-1,2,4-oxadiazol-3-yl)biphenyl-4-carboxamide A solution of N-[3-(2'-methylaminoethylthio)-4-methoxyphenyl]-2'-methyl-4'-(5-methyl-1,2,4-oxadiazol-3-yl)biphenyl-4-carboxamide (E25) (181 mg) in chloroform (3.5 ml) was treated with 85% m-chloroperoxybenzoic acid (72 mg) at –78° C. under argon. The mixture was allowed to warm to room temperature and was stirred for ½ h, then quenched with sodium bicarbonate solution, and extracted into chloroform. The organic phase was dried (Na$_2$SO$_4$) and chromatographed on silica, eluting with chloroform and methanol, to give the title compound as a white solid (28 mg, 15%) Mp 204°–6° C.

$^1$H NMR (250 MHz, CDCl$_3$) δ(ppm): 9.16 (s, 1H), 8.46 (d, 1H), 8.1–8.01 (m, 3H), 7.97 (d, 1H), 7.31 (s, 1H), 7.5 (d, 2H), 7.39 (d, 1H), 6.97 (d, 1H), 3.89 (s, 3H), 2.92–2.76 (m, 2H), 2.7 (s, 3H), 2.49–2.3 (m, 5H), 2.2 (s, 6H).

EXAMPLE 27
N-[5-(2-Dimethylaminoethoxy)-2-chlorophenyl]-2'-methyl-4'-(5-methyl-1,2,4-oxadiazol-3-yl)biphenyl-4-carboxamide (E27)

A solution of N-[3-(2dimethylaminoethoxy)phenyl]-2'-methyl-4'-(5-methyl-1,2,4-oxadiazol-3-yl)biphenyl-4-carboxamide (E13) (200 mg) in dichloromethane (10 ml) was treated with N-chlorosuccinimide (64 mg) and the mixture stirred at room temperature overnight. The reaction mixture was evaporated under reduced pressure, and the residue triturated with diethyl ether and the precipitated succinimide was removed by filtration. The filtrate was evaporated under reduced pressure and flash column chromatographed on silica gel, eluting with dichloromethane, then chloroform and methanol to give the title compound. (77 mg, 36%). Mp 101°–2° C.

$^1$H NMR (200 MHz, CDCl$_3$) δ(ppm): 8.5 (s, 1H), 8.33 (s, 1H), 8.04–7.91 (m, 4H, 7.5 (d, 2H), 7.36 (d, 1H), 7.30 (d, 1H), 6.7 (s, 1H), 4.12 (t, 2H), 2.75 (t, 2H), 2.69 (s, 3H), 2.35 (s, 9H).

EXAMPLE 28
N-[3-(2-Dimethylaminoethoxy)-4-chlorophenyl]-2'-methyl-4'-(5-methyl-1,2,4-oxadiazol-3-yl)biphenyl-4-carboxamide (E28)

The title compound was prepared from 2'-methyl-4'-(5-methyl-1,2,4-oxadiazol-3-yl)biphenyl-4-carboxylic acid (EP 0533268A1) and 3-(2dimethylamioethoxy)-4-chloroaniline (D58) using a similar procedure to Example 1 (72%) mp 159.5°–161° C.

$^1$H NMR (250 MHz, CDCl$_3$) δ(ppm): 8.0 (s, 1H), 7.99–7.9 (m, 4H), 7.7 (s, 1H), 7.47 (d, 2H), 7.38–7.3 (m, 2H), 6.99 (d, 1H), 4.19 (t, 2H), 2.82 (t, 2H), 2.7 (s, 3H), 2.39 (s, 6H), 2.34 (s, 3H).

EXAMPLE 29
N-[3-(2-Dimethylaminoethoxy)-4-bromophenyl]-2'-methyl-4'-(5-methyl-1,2,4-oxadiazol-3-yl)biphenyl-4-carboxamide (E29)

The title compound was prepared from 2'-methyl-4'-(5-methyl-1,2,4-oxadiazol-3-yl)biphenyl-4-carboxylic acid (EP 0533268A1) and 3-(2-dimethylaminoethoxy)-4-bromoaniline (D60) using a similar procedure to Example 1 (64%). Mp 138°–140° C.

$^1$H NMR (250 MHz, CDCl$_3$) δ(ppm): 8.02–7.9 (m, 5H), 7.66 (s, 1H), 7.52–7.42 (m, 3H), 7.34 (d, 1H), 6.95 (d, 1H), 4.19 (t, 2H), 2.83 (t, 2H), 2.69 (s, 3H), 2.49 (s, 6H), 2.32 (s,3H).

EXAMPLE 30
N-[3-(2-Dimethylaminoethoxy)-4-iodophenyl]-2'-methyl-4'-(5-methyl-1,2,4-oxadiazol-3-yl)biphenyl-4-carboxamide (E30)

The title compound was prepared from 2'-methyl-4'-(5-methyl-1,2,4-oxadiazol-3-yl)biphenyl-4-carboxylic acid (EP0533268A1) and 3-(2-dimethylaminoethoxy)-4-iodoaniline (D50) using a similar procedure to Example 20 (0.4 g, 28%). The free-base was converted to the oxalate salt. mp 219°–221° C.

$^1$H NMR (free-base) (200 MHz, CDCl$_3$) δ(ppm): 8.06–7.9 (m, 5H), 7.72 (d, 1H), 7.6 (s, 1H), 7.49 (d, 2H), 7.35 (d, 1H), 6.85 (d, 1H), 4.2 (t, 2H), 2.85 (t, 2H),2.69 (s, 3H), 2.4 (s, 6H), 2.35 (s, 3H)

EXAMPLE 31
N-[3-(2-Dimethylaminoethoxy)-4-ethylphenyl]-2'-methyl-4'-(5-methyl-1,2,4-oxadiazol-3-yl)biphenyl-4-carboxamnide (E31)

The title compound was prepared from 2'-methyl-4'-(5-methyl-1,2,4-oxadiazol-3-yl)biphenyl-4-carboxylic acid (EP 0533268A1) and 3-(2-dimethylaminoethoxy)-4-ethylaniline (D53) using a similar procedure to Example 1, as an off white solid (95%) Mp 126°–7° C.

$^1$H NMR (250 MHz, CDCl$_3$) δ(ppm): 8.01 (s, 1H), 7.99–7.88 (m, 4H), 7.5–7.43 (m, 3H), 7.35 (d, 1H), 7.12 (d, 1H), 6.99 (d, 1H), 4.15 (t, 2H), 2.8 (t, 2H), 2.7–2.59 (m, 5H), 2.36 (s, 6H), 2.34 (s, 3H), 1.20 (t, 3H)

EXAMPLE 32
N-[3-(2-Dimethylaminoethoxy)-4-isopropylphenyl]-2'-methyl-4'-(5-methyl-1,2,4-oxadiazol-3-yl)biphenyl-4-carboxamide (E32)

The title compound was prepared from 2'-methyl-4'-(5-methyl-1,2,4-oxadiazol-3-yl)biphenyl-4-carboxylic acid (EP0533268A1) and 3-(2-dimethylaminoethoxy)-4-isopropylaniline (D56) using a similar procedure to Example 20 (89%). The freebase was converted to the oxalate salt mp 219°–223° C.

$^1$H NMR (free base) (200 MHz, CDCl$_3$) δ(ppm): 8.02–7.85 (m, 5H), 7.51–7.42 (m, 3H), 7.34 (d, 1H), 7.19 (d, 1H), 7.01 (d, 1H), 4.16 (t, 2H), 3.4–3.24 (m, 1H) 2.82 (t,2H), 2.69 (s, 3H), 2.4 (s, 6H), 2.34 (s, 3H), 1.24 (s, 3H), 1.2 (s, 3H).

EXAMPLE 33

N-[3-(2-Dimethylaminoethoxy)-4-methoxyphenyl]-4'-(1,2,4-triazol-1-yl)-2'-methyl-(1,1'-biphenyl)-4-carboxamide The title compound was prepared from 4'-(1,2,4-triazol-1-yl)-2'-methyl-1,1'-biphenyl-4-carboxylic acid (D64, 210 mg) and 3-(2-dimethylaminoethoxy)-4-methoxyaniline (D2, 158 mg) using a similar procedure to Example 20, and isolated as the hydrochloride salt as a white solid (150 mg, 39%), Mp 195°–197° C.

$^1$H NMR (HCl salt) (270 MHz, d$^6$DMSO) δ(ppm): 10.6 (br s, 1H), 10.3 (s, 1H), 8.3 (s, 1H), 8.1 (d, 2H), 7.4–7.7 (m, 6H), 7.05 (d, 1H), 4.33 (t, 2H), 3.8 (s, 3H), 3.55 (m, 2H), 2.9 (2×s, 6H), 2.38 (s, 3H).

EXAMPLE 34

N-[3-(2-Dimethylaminoethoxy)-4-methoxyphenyl]-4'-(5-methyl-1,2,4-oxadiazol-3-yl)-1,1'-biphenyl-4-carboxamide The title compound was prepared from 4'-(5-methyl-1,2,4-oxadiazol-3-yl)-1,1'-biphenyl-4-carboxylic acid (D65, 100 mg) and 3-(2-dimethylaminoethoxy)-4-methoxyaniline (D2, 77 mg) using a similar procedure to Example 20 as a fawn solid (130 mg, 77%) Mp 243°–245° C.

$^1$H NMR (400 MHz, CDCl$_3$) δ(ppm): 8.18 (d, 2H), 7.98 (d, 2H), 7.90 (s, 1H), 7.75–7.80 (m, 4H), 7.5 (s, 1H), 7.12 (dd, 1H), 6.89 (d, 1H), 4.22 (t, 2H), 3.86 (s, 3H), 2.9 (t,2H), 2.7 (s, 3H), 2.45 (s, 6H).

EXAMPLE 35

N-[3-(2-Dimethylaminoethoxy)-4-methoxyphenyl]-4'-(1,2,4-triazol-1-yl)-1,1'-biphenyl-4-carboxamide The title compound was prepared from 4'-(1,2,4-triazol-1-yl)-1,1'-biphenyl-4-carboxylic acid (D69, 191 mg) and 3-(2-dimethylaminoethoxy)-4-methoxyaniline (D2, 151 mg) using a similar procedure to Example 20 and isolated as the hydrochloride salt as a beige solid (85 mg, 24%). Mp 249°–251° C.

$^1$H NMR (HCl salt) (270 MHz, d$^6$DMSO) δ(ppm): 10.8 (s, 1H), 10.3 (s, 1H), 9.42 (s, 1H), 8.3 (s, 1H), 7.85–8.15 (m, 8H), 7.64 (d, 1H), 7.32 (dd, 1H), 7.03 (d, 1H), 4.35 (t, 2H), 3.8 (s, 3H), 3.54 (m, 2H), 2.9 (2×s, 6H).

EXAMPLE 36

N-[3-(2-Dimethylaminoethoxy)-4-methoxyphenyl]-4'-(tetrazol-2-yl)-1,1'-biphenyl-4-carboxaminde The title compound was prepared from 4'-(tetrazol-2-yl)-1,1'-biphenyl-4-carboxylic acid (D73, 150 mg) and 3-(2-dimethylaminoethoxy)-4-methoxyaniline (D2, 118 mg) using a similar procedure to Example 20 as a beige solid (230 mg, 89%). Mp 206°–208° C.

$^1$H NMR (270 MHz, CDCl$_3$) δ(ppm): 8.7 (s, 1H), 8.28 (d, 2H), 8.0 (d, 2H), 7.82–7.9 (m, 4H), 7.48 (s, 1H), 7.1 (dd, 1H), 6.89 (d, 1H), 4.2 (t, 2H), 3.88 (s, 3H), 2.87 (t, 2H), 2.41 (s, 6H)

EXAMPLE 37

N-[3-(2-Dimethylaminoethoxy)-4-methoxyphenyl]-2-methyl-4'-(5-methyl-1,2,4-oxadiazol-3-yl)-1,1'-biphenyl-4-carboxamide The title compound was prepared from 2-methyl-4'-(5-methyl-1,2,4-oxadiazol-3-yl)-1,1'-biphenyl-4-carboxylic acid (D75, 194 mg) and 3-(2-dimethylaminoethoxy)-4-methoxyaniline (D2, 210 mg) using a similar procedure to Example 20 and isolated as the hydrochloride salt as a white solid (160 mg, 30%). Mp 222°–225° C.

$^1$H NMR (HCl salt) (250 MHz, d$^6$DMSO) δ(ppm): 10.25 (s, 1H), 10.1 (br s, 1H), 8.1 (d, 2H), 7.85–7.95 (m, 2H), 7.58–7.7 (m, 3H), 7.36–7.45 (m, 2H), 7.05 (d, 1H), 4.30 (t, 2H), 3.8 (s, 3H), 3.5 (t, 2H), 2.9 (s, 6H), 2.7 (s, 3H), 2.4 (s, 3H)

EXAMPLE 38

N-[3-(2-Dimethylaminoethoxy)-4-methoxyphenyl]-2-methyl-4'-(2-pyridyl)-1,1'-biphenyl-4-carboxamide The title compound was prepared from N-[3-(2-dimethylaminoethoxy)-4-methoxyphenyl]-4-bromo-3-methylbenzamide (163 mg) and 4-(2-pyridyl)phenylboronic acid (D77, 154 mg) using the same procedure as in Description 15 and isolated as a white solid (171 mg, 89%). Mp 149°–151° C.

$^1$H NMR (250 MHz, CDCl$_3$) δ(ppm): 72 (d, 1H), 8.1 (d, 2H), 7.7–7.9 (m, 5H), 7.2–7.55 (m, 5H), 7.06 (dd, 1H), 6.85 (d, 1H), 4.18 (t, 2H), 3.89 (s, 3H), 2.8 ( t, 2H), 2.4 (s, 3H), 2.35 (s, 6H)

EXAMPLE 39

N-[3-(2-Dimethylaminoethoxy)-4-methoxyphenyl]2-methyl-4'-(3-pyridyl)-1,1'-biphenyl)-4-carboxamide The title compound was prepared from N-[3-(2-dimethylaminoethoxy)-4-methoxyphenyl]-4-bromo-3-methylbenzamide (266 mg) and 4-(3-pyridyl)-phenylboronic acid (D79, 130 mg) using the same procedure as in Description 15 and isolated as the hydrochloride salt (130 mg, 38%). Mp 145°–147° C.

$^1$H NMR (HCl salt) (270 MHz, d$^6$DMSO) δppm): 10.42 (br s, 1H), 10.2 (s, 1H), 9.2 (br s, 1H) 8.8 (br d, 1H), 8.65 (d, 1H), 7.85–8.0 (m, 5H), 7.55–7.68 (m, 3H), 7.4 (m, 2H), 7.05 (d, 1H), 4.35 (t, 2H), 3.8 (s, 3H), 3.55 (m, 2H), 2.9 (2×s, 6H), 2.4 (s, 3H).

EXAMPLE 40

N-[3-(2-Dimethylaniinoethoxy)-4-methoxyphenyl]-2'-ethyl-4'-(5-methyl-1,2,4-oxadiazol-3-yl)-1,1'-biphenyl-4-carboxamide The title compound was prepared from 2'-ethyl-4'-(5-methyl-1,2,4-oxadiazol-3-yl)-1,1'-biphenyl-4-carboxylic acid (D82, 250 mg) and 3-(2-dimethylaminoethoxy)-4-methoxyaniline (D2, 170 mg) using a similar procedure to Example 20 and isolated as the hydrochloride salt. MP 178°–180° C.

$^1$H NMR (HCl salt) (270 MHz, d$^6$DMSO) δ(ppm): 10.5 (br s, 1H), 10.3 (s, 1H), 8.08 (d, 2H), 8.0 (s, 1H), 7.9 (d, 1H), 7.65 (d, 1H), 7.55 (d, 2H), 7.35–7.45 (m, 2H), 7.05 (d, 1H), 4.35 (t, 2H), 3.8 (s, 3H), 3.55 (t, 2H), 2.9 (s, 6H), 2.8 (s, 3H), 2.75 (q, 2H), 1.1 (t, 3H).

EXAMPLE 41

N-[3-(2-Dimethylaninoethoxy)-4-methoxyphenyl]-2,2'-dimethyl-4'-(5-methyl-1,2,4-oxadiazol-3-yl)-1,1'-biphenyl-4-carboxamide The title compound was prepared from 2,2'-dimethyl-4'-(5-methyl-1,2,4-oxadiazol-3-yl)-1,1-biphenyl-4-carboxylic acid (D83, 740 mg) and 3-(2-dimethylaminoethoxy)-4-methoxyaniline (D2, 504 mg) using a similar procedure to Example 20 and isolated as the hydrochloride salt (490 mg, 39%). Mp 130°–132° C.

$^1$H NMR (HCl salt) (270 MHz, d$^6$DMSO) δ(ppm): 10.6 (br s, 1H), 10.25 (s, 1H), 7.8–8.0 (m, 4H), 7.62 (d, 1H), 7.40 (dd, 1H), 7.2–7.3 (m, 2H), 7.02 (d, 1H), 4.35 (t, 2H),3.8 (s, 3H), 3.55 (t, 2H), 2.9 (s, 6H), 2.8 (s, 3H), 2.1 (s, 6H)

EXAMPLE 42

N-[3-(N'-(2-Dimethylaminoethyl)-N'-methylanino)-4-methoxyphenyl]-2'-methyl-4'-(5-methyl-1,2,4-oxadiazol-3-yl)-1,1'-biphenyl-4-carboxamide The title compound was prepared from N-(5-amino-2-methoxyphenyl)-N,N',N'-trimethylethylenediamnine (D89) using procedure similar to that of Example 20, followed by conversion to the oxalate salt, as a white solid (51%), m.p. 174°–8° C.

¹H NMR (oxalate salt) (250 MHz, d⁶DMSO) δ(ppm): 10.21 (s, 1H), 8.06 (d, 2H), 7.97 (s, 1H), 7.92 (d, 1H), 7.56 (d, 2H), 7.45 (m, 3H), 6.96 (d, 1H), 3.82 (s, 3H), 3.25 (bs, 4H), 2.79 (s, 6H), 2.72 (s, 3H), 2.68 (s, 3H), 2.35 (s, 3H).

EXAMPLE 43

N-[3-(N'-(2-Dimethylaminoethoxy)-N'-phenethylamino)-4-methoxyphenyl]-2'-methyl-4'-(5-methyl-1,2,4-oxadiazol-3-yl)-1,1'-biphenyl-4-carboxamide The title compound was prepared from N-[2-methoxy-5-nitrophenyl]-phenylacetamide (D90) following a similar procedure to Descriptions 85–89 and Example 42.

¹H NMR (200 MHz, CDCl₃) δ(ppm): 9.25(s,1H), 8.22 (d, 2H), 8.00–7.88 (m, 3H), 7.69 (d, 1H), 7.44 (d, 2H), 7.33 (d, 1H), 7.30–7.10 (m, 5H), 6.90 (d, 1H), 3.86 (s, 3H), 3.62–3.52 (m, 2H), 3.47–3.36 (m, 2H), 3.07–2.95 (m, 2H), 2.84–2.70 (m, 2H), 2.72 (s, 6H), 2.68 (s, 3H), 2.33 (s, 3H).

EXAMPLE 44

N-[3-(N'-(2-Dimethylaminoethoxy)-N'-butylamino)-4-methoxyphenyl]-2'-methyl-4'-(5-methyl-1,2,4-oxadiazol-3-yl)-1,1'-biphenyl-4-carboxamide The title compound was prepared from 2-methoxy-5-nitroaniline and butyryl chloride following a similar procedure to Descriptions 90, 85–89 and Example 42.

¹H NMR (250 MHz, CDCl₃) δ(ppm): 8.62 (br s, 1H), 8.10 (d, 2H), 8.02–7.93 (m, 2H), 7.69 (d, 1H), 7.52–7.44 (m, 3H), 7.36 (d, 1H), 6.88 (d, 1H), 3.86 (s, 3H), 3.50–3.40 (m, 2H), 3.20–3.10 (m, 2H), 2.85–2.75 (m, 2H), 2.68 (s, 3H), 2.55 (s, 6H), 2.35 (s, 3H), 1.55–1.20 (m, 4H), 0.90 (t, 3H).

EXAMPLE 45

3-(2-Dimethylaminoethoxy)-4-methoxy-N-2'methyl-4'-(5-methyl-1,2,4-oxadiazol-3-yl) [1,1'-biphenyl]-4-benzamide The product from description 92 (0.104 g, 0.392 mmol) was dissolved in dry toluene (5 ml) and was treated with trimethylaluminium (2.0M in toluene) (0.785 ml, 1.570 mmol) with stirring under argon. After 0.25 h, a solution of the product from description 2 (0.099 g, 0.392 mmol) in toluene (5 ml) was added. The mixture was then heated to 80° C. After 8 h, the reaction mixture was allowed to cool and was poured into a slurry of silica gel (~5 g) in dichloromethane (20 ml). The slurry was filtered and was then washed with 20% MeOH in CH₂Cl₂ (4×25 ml). The filtrate was then evaporated under reduced pressure to give a yellow oil, which was dried in vacuo. The oil was purified by SiO₂ chromatography (5% MeOH/CH₂Cl₂) as eluant) to give the title compound as a colourless oil (0.095 g, 50%) which was converted to its oxalate salt. m.pt. 203°–205° C.

¹H NMR (250 MHz, CDCl₃) (free base) δ: 7.95 (m, 3H), 7.71 (d, 2H), 7.57 (d, 1H), 7.48 (dd, 1H), 7.35 (m, 3H), 6.92 (d, 1H), 4.32 (t, 2H), 3.91 (s, 3H), 2.89 (t, 2H), 2.70 (s, 3H), 2.41 (s, 6H), 2.38 (s, 3H).

EXAMPLE 46

N-[3-(2-Dimethylaminoethoxy)-4-methoxyphenol]-4'-(1,2,4-triazol-1-yl)-(1,1'-biphenyl)-4-carboxamide 4'-(1,2,4-Triazol-1-yl)-(1,1'-biphenyl)-4-carboxylic acid (191 mg, 0.72 mmol) was heated at reflux with thionyl chloride (2 ml) and toluene (40 ml) for 2 h, and then evaporated to dryness under reduced pressure. 4-Methoxy-3-(2-dimethylaninoethoxy)phenylamine (260 mg, 1.2 mmol) in dry dichloromethane (40 ml) was added with triethylamine (2 ml) and the mixture stirred for 1 h. The solution was partitioned between dichloromethane (40 ml) and saturated aqueous potassium carbonate (40 ml), the organic solution dried (sodium sulphate) and evaporated to dryness under reduced pressure to afford an oil, which was purified by column chromatography (silica, chloroform, methanol 5%) to afford the title compound (173 mg, 53%) which was crystallised from methanol/diethyl ether as the dihydrochloride salt.

¹H NMR (d₆DMSO) δ 2.90 (6H, d), 3.52 (2H, q), 3.79 (3H, s), 4.35 (2H, q, CH₂), 7.02 (1H, d), 7.42 (1H, dd), 7.65 (1H, d), 7.92 (2H, d), 8.02 (4H, q), 8.12 ( 2H, d), 8.30 (1H, s), 9.43 (1H, s), 10.30 (1H, s, NH).

EXAMPLE 47

N-[3-(2-Dimethylaminoethoxy)-4-methoxyphenol]-4'-(tetrazol-2-yl)-(1,1'-biphenyl)-4-carboxamide 4'-(Tetrazol-2-yl)-(1,1'-biphenyl)-4-carboxylic acid (150 mg, 0.56 mmol) was heated at reflux with thionyl chloride (2 ml) and toluene (40 ml) for 2 h, and then evaporated to dryness under reduced pressure. 4-Methoxy-3-(2-dimethylaminoethoxy)phenylamine (118 mg, 0.56 mmol) in dry dichloromethane (40 ml) was added with triethylamine (2 ml) and the mixture stirred for 1 h. The solution was partitioned between dichloromethane (40 ml) and saturated aqueous potassium carbonate (40 ml), the organic solution dried (sodium sulphate) and evaporated to dryness under reduced pressure to afford an oil, which was purified by column chromatography (silica, chloroform./methanol 5%) to afford the title compound (232 mg, 93%).

¹H NMR (d₆DMSO) δ 2.41 (6H, s), 2.88 (2H, t), 3.89 (3H, s), 4.21 (2H, t, CH₂), 6.89 (1H, d), 7.11 (1H, dd), 7.49 (1H, s), 7.80 (4H, m), 8.00 (2H, d), 8.28 (2H, m), 8.70 (1H, s).

EXAMPLE 48

N-[3-(2-Dimethylaminoethoxy)-4-methoxyphenol]-2'-methyl-4'-(1,2,4-triazol-1-yl)-(1,1'-biphenyl)-4-carboxamide 2-Methyl-4-(1,2,4-triazol-1-yl)bromobenzene (200 mg, 0.84 mmol), 4-carboxlic acidbenzene boronic acid (139 mg, 0.84 mmol), sodium carbonate (356 mg, 4 eq), tetrakis (triphenylphosphine)palladium(0) (50 mg) in DME (18 ml) and water (18 ml) was heated under argon at reflux for 24 h, cooled, evaporated to dryness under reduced pressure, partitioned between saturated aqueous sodium carbonate solution (50 ml) and ethyl acetate (50 ml), the aqueous extracts acidified with conc. HCl and dried in vacuo to afford 2-methyl-4'-(1,2,4-triazol-1-yl)-(1,1'-biphenyl)-4-carboxylic acid as a pale yellow crystalline solid (156 mg, 67%).

2-Methyl-4'-(1,2,4-triazol-1-yl)-(1,1'-biphenyl)-4-carboxylic acid (210 mg, 0.75 mmol) was heated at reflux with thionyl chloride (2 ml) and toluene (40 ml) for 2 h, and then evaporated to dryness under reduced pressure. 4-Methoxy-3-(2-dimethylaminoethoxy)phenylamine (158 mg, 0.75 mmol) in dry dichloromethane (40 ml) was added with triethylamine (2 ml) and the mixture stirred for 1 h. The solution was partitioned between dichloromethane (40 ml) and saturated aqueous potassium carbonate (40 ml), the organic solution dried (sodium sulphate) and evaporated to dryness under reduced pressure to afford an oil, which was purified by column chromatography (silica, chloroform,/ methanol 5%) to afford the title compound (388 mg, 100%) which was crystallised from methanol/diethyl ether as the hydrochloride salt.

¹H NMR (d₆DMSO) δ 2.38 (3H, s),2.90 (6H, d), 3.54 (2H, q), 3.80 (3H, s), 4.38 (2H, q, CH₂), 4.80 (bs), 7.03 (1H, d), 7.43 (2H, m), 7.58 (3H, m), 7.81 (1H, d), 8.08 (2H, d), 8.30 (1H, s), 9.38 (1H, s), 10.30 (1H, s).

We claim:

1. A compound of formula (I) or a salt thereof:

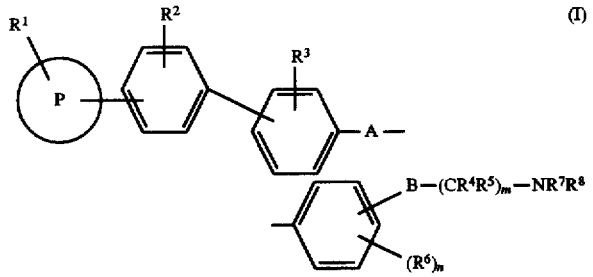

wherein P is oxadiazolyl;

$R^1$, $R^2$ and $R^3$ are independently hydrogen, halogen, $C_{1-6}$ alkyl, $C_{3-6}$ cycloalkyl, $C_{1-6}$ cycloalkenyl, $C_{1-6}$ alkoxy, hydroxy$C_{1-6}$ alkyl, $C_{1-6}$ alkylO$C_{1-6}$ alkyl, alkanoyl, optionally substituted phenyl, alkanoyloxy, hydroxy, nitro, trifluoromethyl, cyano, $CO_2R^9$, $CONR^{10}R^{11}$ where $R^9$, $R^{10}$ and $R^{11}$ are independently hydrogen or $C_{1-6}$ alkyl;

$R^4$ and $R^5$ are independently hydrogen or $C_{1-6}$ alkyl;

$R^6$ is hydrogen, halogen, hydroxy, $C_{1-6}$ alkyl or $C_{1-6}$ alkoxy $R^7$ and $R^8$ are independently hydrogen, $C_{1-6}$ alkyl, optionally substituted phenylalkyl, or together with the nitrogen atom to which they are attached form an optionally substituted 5- to 7-membered heterocyclic ring containing one or two heteroatoms selected from oxygen, nitrogen or sulphur;

A is CONH or NHCO;

B is oxygen, S(O)p where p is 0,1 or 2, or B is $CR^4=CR^5$ or $CR^4R^5$ where $R^4$ and $R^5$ are independently hydrogen or $C_{1-6}$ alkyl;

m is $R^1$, $R^2$ and $R^3$ are independently hydrogen, halogen, $C_{1-6}$ alkyl, $C_{3-6}$ cycloalkyl, $C_{3-6}$ cycloalkenyl, 1 to 4; and n is 1 or 2.

2. A compound according to claim 1 in which P is oxadiazole.

3. A compound according to claim 2 in which $R^1$ and $R^2$ are $C_{1-6}$alkyl.

4. A compound according to claim 1 in which $R^3$ is hydrogen.

5. A compound according to claim 1 in which B is oxygen or, $CH_2$.

6. A compound according to any one of claim 1 in which m is 2 and $R^7$ and $R^8$ are both $C_{1-6}$alkyl.

7. A compound according to claim 1 which is:

N-[3-(Dimethylaminoethoxy)-4-methoxyphenyl]-2'-methyl-4'-(5-methyl-1,2,4-oxadiazol-3-yl)biphenyl-4-carboxamide, N-[3-(2-Diethylaminoethoxy)-4-methoxyphenyl]-2'methyl-4'-(5-methyl-1,2,4-oxadiazol-3-yl)biphenyl-4-carboxamide, N-[3-(2-Diisopropylaminoethoxy)-4-methoxyphenyl]-2'-methyl-4'-(5-methyl-1,2,4-oxadiazol-3-yl)biphenyl-4-carboxamide, N-[3-(2-Dimethylamino-1-methylethoxy)-4-methoxyphenyl]-2'-methyl-4'-(5-methyl-1,2,4-oxadiazol-3-yl)biphenyl-4-carboxamide, N-[3-(2-Dimethylaminopropoxy)-4-methoxyphenyl]-2'-methyl-4'-(5-methyl-1,2,4-oxadiazol-3-yl)biphenyl-4-carboxamide, N-[3-(2-Methylaminoethoxy)-4-methoxyphenyl]-2'-methyl-4'-(5-methyl-1,2,4-oxadiazol-3-yl)biphenyl-4-carboxamide, N-[3-(2-Aminoethoxy)-4-methoxyphenyl]-2'-methyl-4'-(5-methyl-1,2,4-oxadiazol-3-yl)biphenyl-4-carboxamide, N-[3-(2-Piperidin-1-ylethoxy)-4-methoxyphenyl]-2'-methyl-4'-(5-methyl-1,2,4-oxadiazol-3-yl)biphenyl-4-carboxamide, N-[3-(2-Morpholin-4-ylethoxy)-4-methoxyphenyl]-2'-methyl-4'-(5-methyl-1,2,4-oxadiazol-3-yl)biphenyl-4-carboxamide, N-[3-(2-Dimethylaminoethoxy)-4-methoxyphenyl]-2'-methyl-4'-(3-methyl-1,2,4-oxadiazol-5-yl)biphenyl-4-carboxamide, N-[3-(2-Dimethylaminoethoxy)-4-methoxyphenyl]-2'-methyl-4'-(5-methyl-1,3,4-oxadiazol-2-yl)biphenyl-4-carboxamide, N-[3-(2-Dimethylaminoethoxy)-4-methoxyphenyl]-2'-methyl-4'-(1,3,4-oxadiazol-2-yl)biphenyl-4-carboxamide, N-[3-(2-Dimethylaminoethoxy)phenyl]-2'-methyl-4'-(5-methyl-1,2,4-oxadiazol-3-yl)biphenyl-4-carboxamide, N-[5-(2-Dimethylaminoethoxy)-2,4-diiodophenyl]-2'-methyl-4'-(5-methyl-1,2,4-oxadiazol-3-yl)biphenyl-4-carboxamide, N-[3-(3-Dimethylaminopropoxy)-4-methoxyphenyl]-2'-methyl-4'-(5-methyl-1,2,4-oxadiazol-3-yl)biphenyl-4-carboxamide, N-[3-(3-Dimethylaminopropyl)-4-methoxyphenyl]-2'-methyl-4'-(5-methyl-1,2,4-oxadiazol-3-yl)biphenyl-4-carboxamide, N-[3-(3-Dimethylaminoprop-1-enyl)-4-methoxyphenyl]-2'-methyl-4'-(5-methyl-1,2,4-oxadiazol-3-yl)biphenyl-4-carboxamide, N-[4-(3-Dimethylamopropoxy)phenyl]-2'-methyl-4'-(5-methyl-1,2,4-oxadiazol-3-yl)biphenyl-4-carboxamide, N-[3-(2-Pyrrolidin-1-ylethoxy)-4-methoxyphenyl]-2'-methyl-4'-(5-methyl-1,2,4-oxadiazol-3-yl) biphenyl-4-carboxamide, N-[3-(2-Dimethylaminoethoxy)-4-methoxyphenyl]-2'-methyl-4'-(5-ethyl-1,2,4-oxadiazol-3-yl)biphenyl-4-carboxamide, N-[3-(2-Dimethylaminoethoxy)-4-methoxyphenyl]-2'-methyl-4'-(5-dimethylamino-1,2,4-oxadiazol-3-yl) biphenyl-4-carboxamide, N-[3-(2-Dimethylaminoethylthio)-4-methoxyphenyl]-2'-methyl-4'-(5-methyl-1,2,4 -oxadiazol-3-yl)biphenyl-4-carboxamide, N-[3-(2-Dimethylaminoethylsulphinyl)-4-methoxyphenyl]-2'-methyl-4'-(5-methyl-1,2,4-oxadiazol-3-yl)biphenyl-4-carboxamide, N-[5-(2-Dimethylaminoethoxy)-2-chlorophenyl]-2'-methyl-4'-(5-methyl-1,2,4-oxadiazol-3-yl)biphenyl-4-carboxamide, N-[3-(2-Dimethylaminoethoxy)-4-chlorophenyl]-2'-methyl-4'-(5-methyl-1,2,4-oxadiazol-3-yl)biphenyl-4-carboxamide, N-[3-(2-Dimethylaminoethoxy)-4-bromophenyl]-2'-methyl-4'-(5-methyl-1,2,4-oxadiazol-3-yl)biphenyl-4-carboxamide, N-[3-(2-Dimethylaminoethoxy)-4-iodophenyl]-2'-methyl-4'-(5-methyl-1,2,4-oxadiazol-3-yl)biphenyl-4-carboxamide, N-[3-(2-Dimethylaminoethoxy)-4-ethylphenyl]-2'-methyl-4'-(5-methyl-1,2,4-oxadiazol-3-yl)biphenyl-4-carboxamide, N-[3-(2-Dimethylaminoethoxy)-4-isopropylphenyl]-2'-methyl-4'-(5-methyl-1,2,4-oxadiazol-3-yl)biphenyl-4-carboxamnide, N-[3-(2-Dimethylaminoethoxy)-4-methoxyphenyl]-4'-(5-methyl-1,2,4oxadiazol-3-yl)-1,1'-biphenyl-4-carboxamide, N-[3-(2-Dimethylaminoethoxy)-4-methoxyphenyl]-2-methyl-4'-(5-methyl-1,2,4-oxadiazol-3-yl)-1,1'-biphenyl-4-carboxamide, N-[3-(2-Dimethylaminoethoxy)-4-methoxyphenyl]-2'-ethyl-4'-(5-methyl-1,2,4-oxadiazol-3-yl)-1,1'-biphenyl-4-carboxamide, N-[3-(2-Dimethylaminoethoxy)-4-methoxyphenyl]-2,2'-dimethyl-4'-(5-methyl-1,2,4-oxadiazol-3-yl)-1,1'-biphenyl-4-carboxamide, N-[3-(N'-(2-Dimethylaminoethoxy)-N'-phenethylamino)-4-methoxyphenyl]-2'-methyl-4'-(5-methyl-1,2,4-oxadiazol-3-yl)-1,1'-biphenyl-4-carboxamide, N-[3-(N'-(2-Dimethylaminoethoxy)-N'-butylamino)-4-methoxyphenyl]-2'-methyl-4'-(5-methyl-1,2,4-oxadiazol-3-yl)-1,1'-biphenyl-4-carboxamide, or pharmaceutically acceptable salts thereof.

8. A process for the preparation of a compound of formula (I) which comprises (a) reaction of a compound of formula (II):

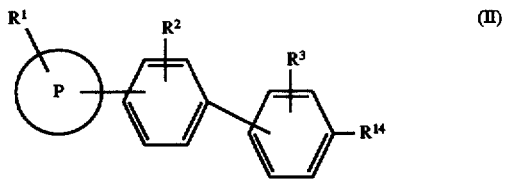

with a compound of formula (III):

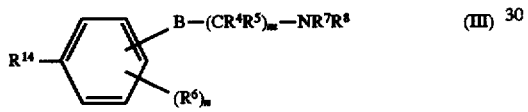

wherein P is oxadiazolyl;

$R^1$, $R^2$ and $R^3$ are independently hydrogen, halogen, $C_{1-6}$ alkyl, $C_{3-6}$ cycloalkyl, $C_{3-6}$ cycloalkenyl, $C_{1-6}$ alkoxy, hydroxy$C_{1-6}$ alkyl, $C_{1-6}$ alkylO$C_{1-6}$ alkyl, alkanoyl, optionally substituted phenyl, alkanoyloxy, hydroxy, nitro, trifluoromethyl, cyano, $CO_2R^9$, $CONR^{10}R^{11}$ where $R^9$, $R^{10}$ and $R^{11}$ are independently hydrogen or $C_{1-6}$ alkyl;

$R^4$ and $R^5$ are independently hydrogen or $C_{1-6}$ alkyl;

$R^6$ is hydrogen, halogen, hydroxy, $C_{1-6}$ alkyl or $C_{1-6}$ alkoxy;

$R^7$ and $R^8$ are independently hydrogen, $C_{1-6}$ alkyl, optionally substituted phenylalkyl, nitrogen atom to which they are attached form an optionally substituted 5- to 7-membered heterocyclic ring containing one or two heteroatoms selected from oxygen, nitrogen or sulphur;

A is CONH or NHCO;

B is oxygen, S(O)p where p is 0,1 or 2, or B is $CR^4=CR^5$ or $CR^4R^5$ where $R^4$ and $R^5$ are independently hydrogen or $C_{1-6}$ alkyl;

m is 1 to 4; and n is 1 or 2, provided that one of $R^{13}$ and $R^{14}$ is an alkanoyl halide or acid anhydride, and one of $R^{13}$ and $R^{14}$ is an amine group, and optionally thereafter in any order:
converting a compound of formula (I) into another compound of formula (I)
forming a pharmaceutically acceptable salt.

9. A pharmaceutical composition comprising from 0.1% to 99% by weight of a compound according to claim 1 in association with a pharmaceutically acceptable carrier or excipient.

* * * * *